US012616680B2

(12) United States Patent
Lucas Lozano et al.

(10) Patent No.: US 12,616,680 B2
(45) Date of Patent: May 5, 2026

(54) COMBINED USE OF BIOTIN AND THIAMINE IN THE TREATMENT OF HUNTINGTON'S DISEASE

(71) Applicants: CONSEJO SUPERIOR DE INVESTIGACIONES CIENTÍFICAS (CSIC), Madrid (ES); CONSORCIO CENTRO DE INVESTIGACIÓN BIOMÉDICA EN RED, Madrid (ES)

(72) Inventors: José Javier Lucas Lozano, Madrid (ES); Sara Picó Del Pino, Madrid (ES); Alberto Parras Rodríguez, Madrid (ES); María Santos Galindo, Madrid (ES)

(73) Assignees: CONSEJO SUPERIOR DE INVESTIGACIONES CIENTÍFICAS (CSIC), Madrid (ES); CONSORCIO CENTRO DE INVESTIGACIÓN BIOMÉDICA EN RED, Madrid (ES)

(*) Notice: Subject to any disclaimer, the term of this patent is extended or adjusted under 35 U.S.C. 154(b) by 964 days.

(21) Appl. No.: 17/763,439

(22) PCT Filed: Sep. 23, 2020

(86) PCT No.: PCT/ES2020/070570
§ 371 (c)(1),
(2) Date: Sep. 8, 2022

(87) PCT Pub. No.: WO2021/058847
PCT Pub. Date: Apr. 1, 2021

(65) Prior Publication Data

US 2023/0026464 A1 Jan. 26, 2023

(30) Foreign Application Priority Data

Sep. 24, 2019 (ES) .................................. 201930825

(51) Int. Cl.
*A61K 31/4188* (2006.01)
*A61K 9/00* (2006.01)
(Continued)

(52) U.S. Cl.
CPC ........ *A61K 31/4188* (2013.01); *A61K 9/0053* (2013.01); *A61K 31/51* (2013.01); *A61P 25/00* (2018.01)

(58) Field of Classification Search
CPC .... A61K 31/4188; A61K 45/06; A61K 31/51; A61K 9/0053; A61K 2300/00; A61P 25/00; A61P 25/28
See application file for complete search history.

(56) References Cited

U.S. PATENT DOCUMENTS 6,746,678 B1 6/2004 Shapiro
2013/0084334 A1* 4/2013 Sedel ...................... A61P 27/02 514/393

FOREIGN PATENT DOCUMENTS

WO 2006053067 A2 5/2006
WO WO-2018220457 A1 * 12/2018 ............. A61K 31/51

OTHER PUBLICATIONS

Pico et al., CPEB alteration and aberrant transcriptome-polyadenylation unveil a treatable SLC19A3 deficiency in Huntington's disease, Science Translational Medicine manuscript, 1-33, Feb. 28, 2012 (Year: 2012).*

(Continued)

*Primary Examiner* — Kortney L. Klinkel
*Assistant Examiner* — Padmaja S Rao
(74) *Attorney, Agent, or Firm* — Bayramoglu Law Offices LLC

(57) ABSTRACT

The present invention relates to the use of a combination of vitamins, more specifically to the combined use of biotin and thiamine, for the treatment of Huntington's disease. More
(Continued)

specifically, the present invention explains that treatment with a combination of biotin and thiamine can improve the neurological, neuroimaging and spectroscopic symptoms associated with Huntington's disease.

9 Claims, 12 Drawing Sheets

Specification includes a Sequence Listing.

(51) Int. Cl.
*A61K 31/51* (2006.01)
*A61P 25/00* (2006.01)

(56) References Cited

OTHER PUBLICATIONS

Frank, Treatment of Huntington's Disease, Neurotherapeutics, vol. 11, 153-160, 2014. (Year: 2014).*
Ross et al., Huntington's disease: from molecular pathogenesis to clinical treatment, Lancet/neurology, vol. 10, 83-98, Jan. 2011. (Year: 2011).*
Al Yamamoto, "Reversal of Neuropathology and Motor Dysfunction in a Conditional Model of Huntington's Disease", Journal, 2000, 57-66, vol. 101, Cell.
Miguel Diaz-Hernandez, "Full Motor Recovery Despite Striatal Neuron Loss and Formation of Irreversible Amyloid-Like Inclusions in a Conditional Mouse of Huntington's Disease", Journal, 2005, 9773-9781, vol. 25, No. 42, The Journal of Neuroscience.
Sarah J. Tabrizi, "Targeting Huntingtin Expression in Patients with Huntington's Disease", Journal, 2019, 2307-2316, vol. 380, No. 24, The New England Journal of Medicine.
Shannon Reagan-Shaw, "Dose Translation from Animal to Human Studies Revisited", Journal, 2007, 659-661, vol. 22, The FASEB Journal.
Laura Mangiarini, "Exon 1 of the HD Gene with an Expanded CAG Repeat is Sufficient to Cause a Progressive Neurological Phenotype in Transgenic Mice", Journal, 1996, 493-506, vol. 87, Cell.
Liliana B. Menalled, "Comprehensive Behavioral and Molecular Characterization of a New Knock-In Mouse Model of Huntington's Disease: zQ175", Journal, 2012, 1-14, vol. 7, No. 12, PLOS One.
Elena Ortiz-Zapater, "Key Contribution of CPEB4-Mediated Translation Control to Cancer Progression", Article, 2012, 83-9, vol. 18, No. 1, Nature Medicine.
Da Wei Huang, "Bioinformatics Enrichment Tools: Paths Toward the Comprehensive Functional Analysis of Large Gene Lists", Journal, 2009, 1-13, vol. 37, No. 1, Nucleic Acids Research.
Maria Pique, "A Combinatorial Code for CPE-Mediated Translation Control", Journal, 2008, 434-448, vol. 132, Cell.
Robert C. Gentleman, "Bioconductor: Open Software Development for Computational Biology and Bioinformatics", Journal, 2004, 1-16, vol. 5, No. 10, Genome Biology.
Robert Gentleman, "Bioinformatics and Computational Biology Solutions Using R and Bioconductor", Book, 2005, 1-478, Springer.
Rafael A. Irizarry, "Use of Mixture Models in a Microarray-Based Screening Procedure for Detecting Differentially Represented Yeast Mutants", Article, 2003, 1-17, vol. 2, No. 1, Statistical Applications in Genetics and Molecular Biology.
Zoltan Szallasi, "Correction of Technical Bias in Clinical Microarray Data Improves Concordance with Known Biological Information", Journal, 2008, 1-8, vol. 9, No. 2, Genome Biological.
Matthew E. Ritchie, "Limma Powers Differential Expression Analyses for RNA-Sequencing and Microarray Studies", Journal, 2015, 1-13, vol. 43, No. 7, Nucleic Acids Research.
Rolf Gruetter, "Automatic, Localized in Vivo Adjustment of All First and Second-Order Shim Coils", Journal, 1993, 804-811, vol. 29, MRM.
Juan Dario Ortigoza-Escobar, "Free-Thiamine is a Potential Biomarker of Thiamine Transporter-2 Deficiency: a Treatable Cause of Leigh Syndrome", Journal, 2016, 31-38, vol. 139, BRAIN—A Journal of Neurology.
Taneli Heikkinen, "Characterization of Neurophysiology and Behavioral Changes, MRI Brain Volumentry and 1H MRS in zQ175 Knock-In Mouse Model of Huntington's Disease", Journal, 2012, 1-15, vol. 7, No. 12, PLOS One.
Brahim Tabarki, "Biotin-Thiamine-Responsive Basal Ganglia Disease", Article, 2013, 1-10, GENE Reviews.
Beata M. Gruber-Bzura, "Role of thiamine in Huntington's disease pathogenesis: In vitro studies", Journal, 2017, 751-760, vol. 26, No. 5, Advances in Clinical and Experimental Medicine.

* cited by examiner

Age: 4 months

(Untreated)

$P = 0.005$

CTRL
zQ175

$n = 12$  11

Age: 7 months (Treated + Untreated)

CTRL H2O     zQ175 H2O     zQ175 B+T

CTRL H$_2$O
CTRL B+T
zQ175 H$_2$O
zQ175 B+T $n = 11$  10  12  15 n.s

CTRL H$_2$O
zQ175 H$_2$O
zQ175 B+T $n = 10$  11  13

```
SEQUENCE LISTING

<160> NUMBER OF SEQ ID NOS: 44

<210> SEQ ID NO 1
<211> LENGTH: 18
<212> TYPE: DNA
<213> ORGANISM: Artificial Sequence
<220> FEATURE:
<223> OTHER INFORMATION: Forward primer of the human CPEB1 gene

<400> SEQUENCE: 1

ggcagccatc ttgaacga                                                    18


<210> SEQ ID NO 2
<211> LENGTH: 20
<212> TYPE: DNA
<213> ORGANISM: Artificial Sequence
<220> FEATURE:
<223> OTHER INFORMATION: Reverse primer of the human CPEB1 gene

<400> SEQUENCE: 2

aagtcacacg accagaacca                                                  20


<210> SEQ ID NO 3
<211> LENGTH: 21
<212> TYPE: DNA
<213> ORGANISM: Artificial Sequence
<220> FEATURE:
<223> OTHER INFORMATION: Forward primer of the human CPEB2 gene

<400> SEQUENCE: 3

gcctcataaa gcagaaagca a                                                21


<210> SEQ ID NO 4
<211> LENGTH: 20
<212> TYPE: DNA
<213> ORGANISM: Artificial Sequence
<220> FEATURE:
<223> OTHER INFORMATION: Reverse primer of the human CPEB2 gene

<400> SEQUENCE: 4

agcatcaatg agtgcctgaa                                                  20


<210> SEQ ID NO 5
```

<211> LENGTH: 25
<212> TYPE: DNA
<213> ORGANISM: Artificial Sequence
<220> FEATURE:
<223> OTHER INFORMATION: Forward primer of the human CPEB3 gene

<400> SEQUENCE: 5
gaacgctact ctagaaaggt gtttg 25

<210> SEQ ID NO 6
<211> LENGTH: 19
<212> TYPE: DNA
<213> ORGANISM: Artificial Sequence
<220> FEATURE:
<223> OTHER INFORMATION: Reverse primer of the human CPEB3 gene

<400> SEQUENCE: 6
cgaaagctgg cagtgatct 19

<210> SEQ ID NO 7
<211> LENGTH: 22
<212> TYPE: DNA
<213> ORGANISM: Artificial Sequence
<220> FEATURE:
<223> OTHER INFORMATION: Forward primer of the human CPEB4 gene

<400> SEQUENCE: 7
cactgtttcc aatggaagat gg 22

<210> SEQ ID NO 8
<211> LENGTH: 20
<212> TYPE: DNA
<213> ORGANISM: Artificial Sequence
<220> FEATURE:
<223> OTHER INFORMATION: Reverse primer of the human CPEB4 gene

<400> SEQUENCE: 8
ggtgaaccca ggccactatg 20

<210> SEQ ID NO 9
<211> LENGTH: 20
<212> TYPE: DNA
<213> ORGANISM: Artificial Sequence
<220> FEATURE:
<223> OTHER INFORMATION: Forward primer of the human AUTS2 gene

<400> SEQUENCE: 9
gaagcggaga gagtccacct 20

<210> SEQ ID NO 10
<211> LENGTH: 23
<212> TYPE: DNA
<213> ORGANISM: Artificial Sequence
<220> FEATURE:
<223> OTHER INFORMATION: Reverse primer of the human AUTS2 gene

<400> SEQUENCE: 10
tcctgaggct taagtgctac atc 23

<210> SEQ ID NO 11
<211> LENGTH: 20
<212> TYPE: DNA
<213> ORGANISM: Artificial Sequence
<220> FEATURE:
<223> OTHER INFORMATION: Forward primer of the human ROCK1 gene

<400> SEQUENCE: 11

-continued tcccctcgaa cgctttctac 20

<210> SEQ ID NO 12
<211> LENGTH: 23
<212> TYPE: DNA
<213> ORGANISM: Artificial Sequence
<220> FEATURE:
<223> OTHER INFORMATION: Reverse primer of the human ROCK1 gene

<400> SEQUENCE: 12
tgtatttttg accactttcc gga 23

<210> SEQ ID NO 13
<211> LENGTH: 29
<212> TYPE: DNA
<213> ORGANISM: Artificial Sequence
<220> FEATURE:
<223> OTHER INFORMATION: Forward primer of the human KTN1 gene

<400> SEQUENCE: 13
atttcagaaa gagagaaaga aataagtgg 29

<210> SEQ ID NO 14
<211> LENGTH: 23
<212> TYPE: DNA
<213> ORGANISM: Artificial Sequence
<220> FEATURE:
<223> OTHER INFORMATION: Reverse primer of the human KTN1 gene

<400> SEQUENCE: 14
tgttcaactg catccttcaa aga 23

<210> SEQ ID NO 15
<211> LENGTH: 22
<212> TYPE: DNA
<213> ORGANISM: Artificial Sequence
<220> FEATURE:
<223> OTHER INFORMATION: Forward primer of the human SLC19A3 gene

<400> SEQUENCE: 15
agttcctgga tttaccccac tg 22

<210> SEQ ID NO 16
<211> LENGTH: 22
<212> TYPE: DNA
<213> ORGANISM: Artificial Sequence
<220> FEATURE:
<223> OTHER INFORMATION: Reverse primer of the human SLC19A3 gene

<400> SEQUENCE: 16
ggttctgagg gtctcatcat gg 22

<210> SEQ ID NO 17
<211> LENGTH: 19
<212> TYPE: DNA
<213> ORGANISM: Artificial Sequence
<220> FEATURE:
<223> OTHER INFORMATION: Forward primer of the human 18S gene

<400> SEQUENCE: 17
atccattgga gggcaagtc 19

<210> SEQ ID NO 18
<211> LENGTH: 20
<212> TYPE: DNA

<213> ORGANISM: Artificial Sequence
<220> FEATURE:
<223> OTHER INFORMATION: Reverse primer of the human 18S gene

<400> SEQUENCE: 18
gctcccaaga tccaactacg 20

<210> SEQ ID NO 19
<211> LENGTH: 20
<212> TYPE: DNA
<213> ORGANISM: Artificial Sequence
<220> FEATURE:
<223> OTHER INFORMATION: Forward primer of the human beta-tubulin gene

<400> SEQUENCE: 19
ctttgtggaa tggatcccca 20

<210> SEQ ID NO 20
<211> LENGTH: 19
<212> TYPE: DNA
<213> ORGANISM: Artificial Sequence
<220> FEATURE:
<223> OTHER INFORMATION: Reverse primer of the human b-tubulin gene

<400> SEQUENCE: 20
gactgccatc ttgaggcca 19

<210> SEQ ID NO 21
<211> LENGTH: 21
<212> TYPE: DNA
<213> ORGANISM: Artificial Sequence
<220> FEATURE:
<223> OTHER INFORMATION: Forward primer of the mouse Cpeb1 gene

<400> SEQUENCE: 21
ttatctgcag ctcacaacct g 21

<210> SEQ ID NO 22
<211> LENGTH: 23
<212> TYPE: DNA
<213> ORGANISM: Artificial Sequence
<220> FEATURE:
<223> OTHER INFORMATION: Reverse primer of the mouse cpeb1 gene

<400> SEQUENCE: 22
gcaaaagtac ttgaagcaga cct 23

<210> SEQ ID NO 23
<211> LENGTH: 20
<212> TYPE: DNA
<213> ORGANISM: Artificial Sequence
<220> FEATURE:
<223> OTHER INFORMATION: Forward primer of the mouse cpeb2 gene

<400> SEQUENCE: 23
ctgcagcaga ggaactcgta 20

<210> SEQ ID NO 24
<211> LENGTH: 20
<212> TYPE: DNA
<213> ORGANISM: Artificial Sequence
<220> FEATURE:
<223> OTHER INFORMATION: Reverse primer of the mouse cpeb2 gene

<400> SEQUENCE: 24
ggttgctcca aggagactgt 20

-continued

```
<210> SEQ ID NO 25
<211> LENGTH: 18
<212> TYPE: DNA
<213> ORGANISM: Artificial Sequence
<220> FEATURE:
<223> OTHER INFORMATION: Forward primer of the mouse cpeb3 gene

<400> SEQUENCE: 25

aaaacccagc cccagtct                                                    18


<210> SEQ ID NO 26
<211> LENGTH: 19
<212> TYPE: DNA
<213> ORGANISM: Artificial Sequence
<220> FEATURE:
<223> OTHER INFORMATION: Reverse primer of the mouse cpeb3 gene

<400> SEQUENCE: 26

gcttggggat ctctgagga                                                   19


<210> SEQ ID NO 27
<211> LENGTH: 24
<212> TYPE: DNA
<213> ORGANISM: Artificial Sequence
<220> FEATURE:
<223> OTHER INFORMATION: Forward primer of the mouse cpeb4 gene

<400> SEQUENCE: 27

caaatcttat tttccaccaa aagg                                             24


<210> SEQ ID NO 28
<211> LENGTH: 22
<212> TYPE: DNA
<213> ORGANISM: Artificial Sequence
<220> FEATURE:
<223> OTHER INFORMATION: Reverse primer of the mouse cpeb4 gene

<400> SEQUENCE: 28

catcaatgag agcctgaaca ga                                               22


<210> SEQ ID NO 29
<211> LENGTH: 20
<212> TYPE: DNA
<213> ORGANISM: Artificial Sequence
<220> FEATURE:
<223> OTHER INFORMATION: Forward primer of the mouse auts2 gene

<400> SEQUENCE: 29

cctccaggcc ctagtctctt                                                  20


<210> SEQ ID NO 30
<211> LENGTH: 20
<212> TYPE: DNA
<213> ORGANISM: Artificial Sequence
<220> FEATURE:
<223> OTHER INFORMATION: Reverse primer of the mouse auts2 gene

<400> SEQUENCE: 30

aaggggtccc agtaggatgt                                                  20


<210> SEQ ID NO 31
<211> LENGTH: 20
<212> TYPE: DNA
<213> ORGANISM: Artificial Sequence
<220> FEATURE:
```

-continued

<223> OTHER INFORMATION: Forward primer of the mouse rock1 gene

<400> SEQUENCE: 31
gatcccaaat cggaagtgaa 20

<210> SEQ ID NO 32
<211> LENGTH: 19
<212> TYPE: DNA
<213> ORGANISM: Artificial Sequence
<220> FEATURE:
<223> OTHER INFORMATION: Reverse primer of the mouse rock1 gene

<400> SEQUENCE: 32
tcataaacca gggcatcca 19

<210> SEQ ID NO 33
<211> LENGTH: 24
<212> TYPE: DNA
<213> ORGANISM: Artificial Sequence
<220> FEATURE:
<223> OTHER INFORMATION: Forward primer of the mouse ktn1 gene

<400> SEQUENCE: 33
ttaaaagctg aagtgcagaa attg 24

<210> SEQ ID NO 34
<211> LENGTH: 19
<212> TYPE: DNA
<213> ORGANISM: Artificial Sequence
<220> FEATURE:
<223> OTHER INFORMATION: Reverse primer of the mouse ktn1 gene

<400> SEQUENCE: 34
acctcatgtg cggtagcag 19

<210> SEQ ID NO 35
<211> LENGTH: 21
<212> TYPE: DNA
<213> ORGANISM: Artificial Sequence
<220> FEATURE:
<223> OTHER INFORMATION: Forward primer of the mouse slc19a3 gene

<400> SEQUENCE: 35
gagcagtaga ggccatagca a 21

<210> SEQ ID NO 36
<211> LENGTH: 21
<212> TYPE: DNA
<213> ORGANISM: Artificial Sequence
<220> FEATURE:
<223> OTHER INFORMATION: Reverse primer of the mouse slc19a3 gene

<400> SEQUENCE: 36
ccttcagata gcccactgag a 21

<210> SEQ ID NO 37
<211> LENGTH: 20
<212> TYPE: DNA
<213> ORGANISM: Artificial Sequence
<220> FEATURE:
<223> OTHER INFORMATION: Forward primer of the mouse 18s gene

<400> SEQUENCE: 37
ctcaacacgg gaaacctcac 20

-continued

<210> SEQ ID NO 38
<211> LENGTH: 20
<212> TYPE: DNA
<213> ORGANISM: Artificial Sequence
<220> FEATURE:
<223> OTHER INFORMATION: Reverse primer of the mouse 18s gene

<400> SEQUENCE: 38
cgctccacca actaagaacg 20

<210> SEQ ID NO 39
<211> LENGTH: 20
<212> TYPE: DNA
<213> ORGANISM: Artificial Sequence
<220> FEATURE:
<223> OTHER INFORMATION: Forward primer of the mouse gapdh gene

<400> SEQUENCE: 39
ctcccactct tccaccttcg 20

<210> SEQ ID NO 40
<211> LENGTH: 24
<212> TYPE: DNA
<213> ORGANISM: Artificial Sequence
<220> FEATURE:
<223> OTHER INFORMATION: Reverse primer of the mouse gapdh gene

<400> SEQUENCE: 40
cataccagga aatgagcttg acaa 24

<210> SEQ ID NO 41
<211> LENGTH: 20
<212> TYPE: DNA
<213> ORGANISM: Artificial Sequence
<220> FEATURE:
<223> OTHER INFORMATION: Forward primer mouse beta-actin gene

<400> SEQUENCE: 41
ctaaggccaa ccgtgaaaag 20

<210> SEQ ID NO 42
<211> LENGTH: 20
<212> TYPE: DNA
<213> ORGANISM: Artificial Sequence
<220> FEATURE:
<223> OTHER INFORMATION: Reverse primer of the mouse beta-actin gene

<400> SEQUENCE: 42
accagaggca tacagggaca 20

<210> SEQ ID NO 43
<211> LENGTH: 21
<212> TYPE: DNA
<213> ORGANISM: Artificial Sequence
<220> FEATURE:
<223> OTHER INFORMATION: Forward primer of the mouse beta-tubulin gene

<400> SEQUENCE: 43
gacctatcat ggggacagtg a 21

<210> SEQ ID NO 44
<211> LENGTH: 20
<212> TYPE: DNA
<213> ORGANISM: Artificial Sequence
<220> FEATURE:
<223> OTHER INFORMATION: Reverse primer of the mouse beta-tubulin gene -continued

```
<400> SEQUENCE: 44

cggctctggg aacatagttt                                              20
```

COMBINED USE OF BIOTIN AND THIAMINE IN THE TREATMENT OF HUNTINGTON'S DISEASE

CROSS-REFERENCE TO RELATED APPLICATIONS AND PRIORITY

This patent application claims priority from PCT Application No. PCT/ES2020/070570 filed Sep. 23, 2020, which claims priority from Spanish Patent Application No. P201930825 filed Sep. 24, 2019. Each of these patent applications are herein incorporated by reference in their entirety.

FIELD OF INVENTION

The present invention belongs to the field of medicine and pharmacy and relates to the use of a combination of vitamins, more specifically to the combined use of biotin and thiamine in the prevention and/or treatment of Huntington's disease (HD).

REFERENCE MATERIALS

Various sequence listings and variant listings are provided herein and attached in a separate sequence listing .txt file. The provided listings are incorporated herein by reference.

BACKGROUND OF THE INVENTION

Huntington's disease is an inherited neurodegenerative disorder characterised by marked atrophy of the striatum (St) and prominent motor symptoms caused by a CAG trinucleotide repeat in the exon 1 coding region of the Huntingtin gene (Htt) on human chromosome 4, giving rise to a self-aggregating polyglutamine (polyQ) segment in the N-terminal region of the Huntingtin protein, which leads to an accumulation of said structurally changed and modified protein and fragments thereof in the brain and other organs or cells over time. In addition to the toxicity of PolyQ, there is also evidence of toxicity induced by the Htt mRNA molecule with CAG expansion.

Clinical symptoms of Huntington's disease progress in a predictable manner, beginning with mood swings or cognitive problems followed by unsteady gait and motor problems which occur as a result of progressive neuronal death in different areas of the brain. This manifests itself with more virulence in the medium spiny neurons of the striatum and determines the onset of impaired motor coordination and typical "chorea" movements. Over time, physical abilities further deteriorate, with evident movement coordination problems in combination with a greater decline in mental abilities and psychiatric and behavioural problems.

Symptoms can vary significantly and it is well documented that age at onset is inversely correlated with the number of CAG repeats in the modified htt gene, corroborating the causative role of modified Huntingtin.

There is no cure or prevention for HD nor is there any known way to stop the disease from getting worse. The average life expectancy is approximately twenty years after the first clinical manifestation. The aim of treatment is to delay and reduce symptoms and to help people with the disease care for themselves for as long as possible.

Studies in genetically modified mouse models of HD have shown that HD-like phenotypes can be resolved by knocking out the expression of the mutant huntingtin gene, even in advanced stages of the disease (Yamamoto et al. Cell. 2000, 101: 57-66; Díaz-Hernández et al. J. Neurosci., 2005, 25:9773-9781). In this sense, gene therapy is an important approach in the search for a possible treatment of the disease. Thus, introducing different gene constructs at the cellular level to inhibit the transcription or translation of the mutated protein, even to replace the defective gene with a new one, through gene therapy has given good results in mouse animal models of the pathology, but unfortunately these trials do not provide the same results in humans since said therapy is not effective in them. This strategy is therefore still far from being an effective strategy for its application in humans (Tabrizi S J. at al. N Engl J Med. 2019; 380(24):2307-2316).

Pharmacological therapy is the most used therapy to relieve the symptoms of subjects suffering from Huntington's disease. In this sense, tetrabenazine is used for the symptomatic treatment of hyperkinetic movement disorders, such as Huntington's disease, hemiballismus, senile chorea, tics, tardive dyskinesia and Tourette's syndrome. The main pharmacological effect of tetrabenazine is to reduce the supply of monoamines (e.g., dopamine, serotonin and norepinephrine) in the central nervous system by inhibiting isoform 2 of the human vesicular monoamine transporter (hVMAT2). The drug also blocks postsynaptic dopamine receptors. Tetrabenazine is an effective and safe drug for the treatment of various hyperkinetic movement disorders and, unlike typical neuroleptic agents, it has not been shown to cause tardive dyskinesia. Nevertheless, tetrabenazine does show a number of dose-related side effects, including depression, Parkinson's disease, drowsiness, nervousness or anxiety, insomnia and, in exceptional cases, neuroleptic malignant syndrome.

The international patent application WO2006053067 describes the use of a combination of amantadine and tetrabenazine for the treatment of hyperkinetic disorders and, in particular, of Huntington's disease. There is a serious side effect of this tetrabenazine drug that triggers or worsens depression and other psychiatric disorders.

Although great progress has been made in recent years in understanding the aetiology, genetics and physiopathology of HD, currently existing therapies are palliative and, moreover, have several side effects. The absence of drugs that act by preventing or significantly delaying the development of diseases of this type means that new alternative therapies that effectively reduce the progression of the disease are required. Therefore, there is still a need for new therapies that can prevent or delay the development of HD.

DESCRIPTION OF THE INVENTION

The inventors have observed that the administration of a vitamin-based combination, preferably a combination of biotin and thiamine, can improve motor symptoms and reducing striatal alterations, particularly by reducing striatal atrophy and increasing phosphocreatine levels associated with Huntington's disease.

Thus, firstly, the inventors observed that the cytoplasmic polyadenylation element binding proteins (CPEB), more specifically the CPEB1 and CPEB4 proteins, responsible for regulating the translation of numerous mRNAs by modifying their poly(A) tail, have an altered expression in the striatum of subjects suffering from HD compared to healthy control subjects (Example 1). The alteration in the levels of these proteins led to the analysis of the level of polyadenylation of the transcriptome in striatal tissue samples from mouse models of HD which show similar alterations in the CPEB1 and CPEB4 levels (Example 2). Said analysis revealed that one of the genes showing greater shortening of the poly(A) tail is the SLC19A3 gene, which encodes for a thiamine transporter, specifically for the ThTr2 transporter (Example 3). A shortening of the poly(A) tail correlates with a lower level of mRNA translation and, therefore, a lower protein level, which led to the suspicion that subjects with HD have a ThTr2 transporter (SLC19A3) deficiency. In fact, this was corroborated in striatal brain samples from subjects with HD, where a decrease in the thiamine transporter SLC19A3 was observed (Example 3).

In the brain, the thiamine transporter SLC19A3 is mainly located in blood vessels and neurons and, as observed in Example 3, the inventors detected a decrease in thiamine in the cerebrospinal fluid (CSF) of subjects with HD. This decrease is fundamentally observed in the form of thiamine monophosphate (TMP), which is the form most commonly found in CSF. Inside cells and tissues, on the other hand, the most common form is thiamine pyrophosphate (TPP), which is the form with a biological role as cofactor for multiple metabolic enzymes, and the inventors observed a decrease in the percentage of TPP in homogenates of striatal tissue samples from subjects with HD.

It is known that subjects suffering from biotin-thiamine-responsive basal ganglia disease (BTBGD) have mutations in the SLC19A3 gene, causing the protein encoded by said gene to not properly fulfil its function, reducing the absorption of thiamine in the cells and with serious consequences for the health of the affected individuals, such as symptoms of encephalopathy (lethargy, stupor, etc.), movement disorders, speech difficulties or loss of speech, swallowing difficulties, epileptic seizures, etc. These symptoms characteristically respond to treatment with high-dose biotin and thiamine, hence the name given to this form of the disease.

As mentioned earlier, the inventors discovered decreased protein levels of SLC19A3 in the striatum of subjects with HD, as well as decreased thiamine levels in the cerebrospinal fluid (total and TMP) and in the brain of said subjects with HD (TPP). These results made the inventors suspect that the administration of a combination of thiamine and biotin-based vitamins would improve the symptoms of HD, since subjects suffering from BBGD respond favourably to the administration of thiamine and biotin because the latter increases the expression of the transporter. Thus, as observed in Example 4, the combined administration of thiamine and biotin in mouse models of HD improves the symptoms of the disease and mitigates morphological and metabolic alterations of the striatum such as atrophy and increased phosphocreatine, which are also associated with the disease. Therefore, the invention relates to the use of a combination of thiamine and biotin for the treatment of HD. This discovery opens a new therapeutic window for the treatment of this pathology that has not been previously contemplated in the state of the art.

Another object of the invention are compositions comprising a combination of thiamine and biotin for use in the treatment of HD. Therefore, the invention also relates to a method for treating a subject suffering from HD, comprising the step of administering a therapeutically effective amount of a combination of thiamine and biotin to said subject.

Thus, in a first aspect, the present invention relates to a composition, preferably a pharmaceutical composition comprising a therapeutically effective concentration of biotin and thiamine for use in the prevention and/or treatment of Huntington's disease. Hereinafter this first aspect of the invention will be referred to as the composition for use of the invention.

The term "composition", "pharmaceutical composition", or "drug", used interchangeably throughout this document, refers to any substance or combination of substances used for the prevention, diagnosis, relief, treatment or cure of diseases in humans or animals. In the context of the present invention, it refers to a composition that can prevent and/or treat HD. The pharmaceutical composition of the invention can be used alone or in combination with other pharmaceutical compositions.

As used in this specification, "treatment", "treat" or "that treats" refers to: (a) the prevention of the onset of the disease or illness in a subject who may be predisposed to the disease or illness but has not yet been diagnosed; (b) the inhibition of the disease or illness, in other words, the interruption of its development; (c) the relief or improvement of the disease or illness, in other words, the induced regression of the disease or illness; or (d) the cure of the disease or illness, in other words, the interruption of its development or progression. The population of subjects treated with the composition of the invention includes those subjects who suffer from the undesirable illness or disease, as well as subjects at risk of developing the illness or disease.

The terms "disorder" and "disease" are used interchangeably to refer to an illness of a subject or individual.

In the present invention, the terms "subject" and "individual" are used interchangeably. As used in this document, the term "subject" or "individual" refers to all animals classified as mammals and includes, among others, farm and domestic animals, primates and humans, for example, human beings, non-human primates, cows, horses, pigs, sheep, goats, dogs, cats or rodents. Preferably, the subject is a human being, man or woman, of any age or race, who suffers from HD.

Biotin (Formula I), also known as vitamin H, vitamin B7 or vitamin B8, is a water-soluble vitamin found naturally in many foods, such as offal, eggs and certain vegetables. In mammals, biotin acts as a cofactor for four metabolic carboxylases involved in several key steps of energy metabolism, including pyruvate carboxylase (gluconeogenesis), 3-methylcrotonyl CoA and propionyl CoA carboxylases (catabolism of certain amino acids which supply the Krebs cycle with intermediate metabolites), and acetyl CoA carboxylase (fatty acid synthesis). Accordingly, the mechanism of action of biotin can be seen as an enhancer of brain energy (ATP) production. There is evidence that biotin can also regulate gene expression through mechanisms independent of its function as a prosthetic group of carboxylases, such as, for example, regulating the transcription of the SLC19A3 gene. Biotin is composed of a ureido (imidazolic) ring fused with a tetrahydrothiophene ring. A substitute valeric acid binds to one of the carbon atoms of the tetrahydrothiophene ring. There are three forms of biotin: free biotin, biocytin (e-biotin-L-Lysine) and two sulfoxides L and D of biotin. The CAS number of biotin is 58-85-5.

Formula I

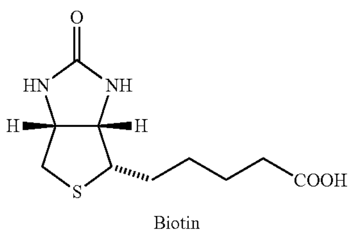

Biotin

For purposes of the present invention, the term "biotin", "vitamin H", "vitamin B7" or "vitamin B8" refers to the biotin compound itself.

Thiamine (Formula II), also known as vitamin B1 or aneurine, is a water-soluble vitamin that is insoluble in alcohol and found naturally in many foods, such as beef, chicken, grains, nuts and beans. Vegetables provide free thiamine, whereas meats mainly provide thiamine diphosphate (TDP, also called thiamine pyrophosphate or TPP). Absorption occurs in the small intestine (jejunum, ileum), it being favoured by the presence of vitamin C and folic acid, but inhibited by the presence of ethanol (ethyl alcohol), it is necessary in the daily diet of most vertebrates and some microorganisms, its deficiency in the human body causes diseases such as beriberi and Korsakoff syndrome. The most common and biologically active form of thiamine is TDP, which acts as a cofactor for numerous metabolic enzymes. The CAS number of thiamine is 59-43-8.

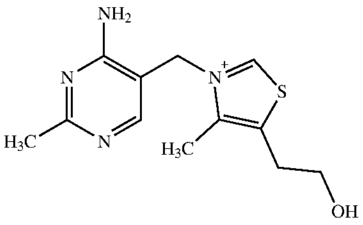

Thiamine

For purposes of the present invention, the term "thiamine" or "vitamin B1" refers to the thiamine compound itself.

The term "therapeutically effective amount" as used herein refers to the amount of a compound or compounds that, when administered, is sufficient to prevent the development of, or to relieve to some degree, one or more symptoms of the disease that it targets. The particular dose of each compound administered according to this invention will of course be determined by the particular conditions surrounding the case, including the compound administered, the route of administration, the particular condition being treated, as well as considerations such as age, weight and sex of the treated subject.

As is well known in the art, therapeutically effective amounts for use in humans can also be determined from animal models. For example, a human dose can be formulated to achieve a concentration that has been found to be effective in animals. Dosage amounts and intervals may be individually adjusted to provide effective levels of the compound administered for the particular clinical indication being treated. This will provide a therapeutic regimen in accordance with the severity of the individual's state of disease. Thus, adjusting the dose to achieve maximum efficacy in humans is well within the capabilities of one skilled in the art. The article by Reagan-Shaw S. "*Dose translation from animal to human studies revisited*". FASEB J 2007, 22:659-661, provides the standard conversion factors used to convert mg/kg to mg/m$^2$. The article also explains that this conversion is the basis for converting the dose in a first animal species to dose in a second animal species (allometric dose translation). Therefore, the animal dose (AD) in mg/kg can be converted to a human equivalent dose (HED) in mg/kg using the following formula:

$$HED(\text{mg/kg}) = AD(\text{mg/kg}) \times \frac{\text{Animal } Km}{\text{Human } Km}$$

where the Km factor for each species is shown in Table 1 (data taken from Reagan-Shaw S. "*Dose translation from animal to human studies revisited*". FASEB J 2007, 22:659-661).

TABLE 1

Km factor for the conversion of AD to HED.

| Species | | Km Factor |
|---|---|---|
| Human | Adult | 37 |
| | Child | 25 |
| Baboon | | 20 |
| Dog | | 20 |
| Monkey | | 12 |
| Rabbit | | 12 |
| Guinea pig | | 8 |
| Rat | | 6 |
| Hamster | | 5 |
| Mouse | | 3 |

Using the teachings provided in this document, an effective therapeutic treatment regimen can be planned that does not cause substantial toxicity and, nevertheless, is effective in treating the clinical symptoms of a subject suffering from HD in particular. This planning should involve careful selection of the active compound, taking into consideration factors such as the potency of the compound, the relative bioavailability, the body weight of the subject, the presence and severity of adverse side effects, the preferred route of administration and the toxicity profile of the selected agent.

In a preferred embodiment, the concentration of biotin in the composition of the invention comprises at least 0.40 mg/kg/day. In a more preferred embodiment, the concentration of biotin in the composition of the invention is selected from the list consisting of: at least 0.40 mg/kg/day, at least 1 mg/kg/day, at least 1.5 mg/kg/day, at least 2 mg/kg/day, at least 2.5 mg/kg/day, at least 3 mg/kg/day, at least 3.5 mg/kg/day, at least 4 mg/kg/day, at least 4.5 mg/kg/day and at least 5 mg/kg/day.

In another preferred embodiment, the concentration of thiamine in the composition of the invention comprises at least 2 mg/kg/day. In a more preferred embodiment, the concentration of thiamine in the composition of the invention is selected from the list consisting of: at least 2 mg/kg/day, at least 2.5 mg/kg/day, at least 3 mg/kg/day, at least 4 mg/kg/day, at least 5 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, at least 50 mg/kg/day, at least 55 mg/kg/day, at least 60 mg/kg/day, at least 85 mg/kg/day, at least 70 mg/kg/day, at least 75 mg/kg/day, at least 80 mg/kg/day, at least 85 mg/kg/day, at least 90 mg/kg/day, at least 95 mg/kg/day and at least 100 mg/kg/day.

In another more preferred embodiment, the composition for use of the invention further comprises at least one excipient and/or pharmacologically acceptable carrier.

In the present invention, the term "excipient" refers to a substance that aids the absorption of any of the components of the composition of the present invention, stabilises said components or aids the preparation of the composition in the sense of giving it consistency or contributing flavours that make it more pleasant. Thus, the excipients may have the function of keeping the components cohesive, such as starches, sugars or celluloses, a sweetening function, a colouring function, a protective function against drugs, such as isolation from air and/or moisture, the function of filling a tablet, capsule or other form of presentation such as, for example, dibasic calcium phosphate, a disintegrating function to facilitate the dissolution of the components and the absorption thereof in the intestine, without excluding any other type of excipient not mentioned herein. Therefore, the term "excipient" is defined as the material included in galenic forms and is added to active ingredients or associations thereof for facilitating its preparation and stability, modifying its organoleptic properties or determining the physicochemical properties of the pharmaceutical composition and its bioavailability. Preferred excipients for use in the present invention include sugars, starches, celluloses, gums and proteins.

Examples of pharmaceutically acceptable carriers are known in the state of the art and include phosphate-buffered saline solutions, water, emulsions, such as oil/water emulsions, different types of wetting agents, sterile solutions, etc. The compositions comprising said carriers can be formulated by conventional procedures known in the state of the art. As used in this specification, the terms "pharmaceutically acceptable", "physiologically tolerable" and grammatical variations thereof, when referring to compositions, supports, diluents and reagents, are used interchangeably and indicate that the materials can be administered to a subject without producing undesirable physiological effects.

In another more preferred embodiment, the active ingredients making up the composition for use of the invention, i.e., biotin and thiamine, are adapted to be administered separately, simultaneously or sequentially, or by juxtaposition, by any convenient route of administration, both in separate or combined compositions.

The term "active ingredient" is understood as any substance or molecule that is biologically active. It is also known as "Active Pharmaceutical Ingredient" or API.

"Separate administration" is understood as the individual administration of each of the active ingredients of the composition of the invention. Said individual administration of each active ingredient can be simultaneous or sequential. Separate administration is understood to be "simultaneous" when the administration of the active ingredients is carried out at the same moment in time. On the contrary, separate administration is understood to be "sequential" when the administration of the active ingredients is carried out at different moments in time, in other words, one active ingredient is first administered and then the other is administered. Thus, in a particular embodiment, the administration of biotin precedes the administration of thiamine or vice versa.

"Juxtaposed administration" is understood as the joint administration of both active ingredients, in other words, biotin and thiamine are administered together in a single composition, which is administered to the subject.

The composition of the invention, as well as the active ingredients that make it up, can be administered by any route of administration. Examples of routes of administration include, without being limited to, the intraperitoneal route, intravenous route, intramuscular route, subcutaneous route, intrathecal route, intraventricular route, oral route, enteral route and parenteral (intravenous) route. In a particular embodiment, the composition of the invention and/or the active ingredients that make it up are administered orally or parenterally, more preferably, orally. Thus, both the composition of the invention and the active ingredients that make it up will be suitably formulated based on the chosen route of administration, such as, for example, in a solid pharmaceutical administration form (e.g., tablets, capsules, coated tablets, granules, suppositories, sterile crystalline or amorphous solids that can be reconstituted to provide liquid forms, etc.) or in a liquid pharmaceutical administration form (e.g., solutions, suspensions, emulsions, elixirs, lotions, ointments etc.), preferably in unit dosage forms suitable for the single administration of measured doses.

In another preferred embodiment, the composition for use of the invention is repeatedly administered to a subject suffering from HD.

In another more preferred embodiment, the composition for use of the invention may additionally comprise at least one active ingredient in addition to those mentioned above.

In a more preferred embodiment, the additional active ingredient that is part of the composition for use of the invention is selected from the list consisting of: tetrabenazine, haloperidol, chlorpromazine, risperidone, quetiapine, amantadine, levetiracetam, clonazepam, citalopram, escitalopram, fluoxetine, sertraline, quetiapine, risperidone, olanzapine, valproate, carbamazepine, lamotrigine and/or any of the combinations thereof.

In another aspect, the present invention also provides methods for preventing and/or treating HD comprising administering a therapeutically effective amount of the composition of the invention to a subject who needs it, as described throughout this document.

Throughout the description and the claims, the word "comprises" and its variants do not intend to exclude other technical features, additives, components or steps. For those skilled in the art, other objects, advantages and features of the invention may be partially deduced from both the description and the embodiment of the invention. The following examples and figures are provided by way of illustration and are not intended to limit the present invention.

EXAMPLES

Figure 1A:
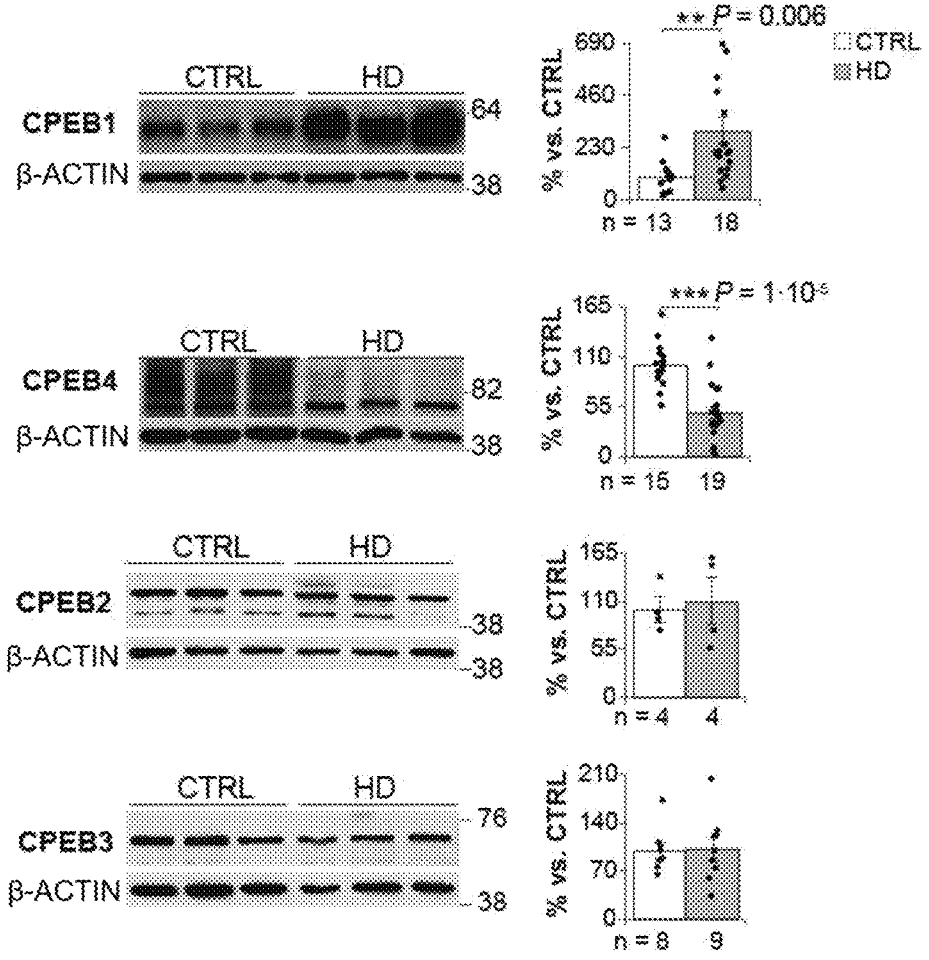
FIG. 1 shows an analysis of the levels of the cytoplasmic polyadenylation element binding proteins 1, 2, 3 and 4 (CPEB1 to 4) at the protein level by Western blot (A, B and E) and at the mRNA level by qRT-PCR (C and D) in the striatum of: subjects suffering from HD (HD) and control subjects (CTRL) (A) (C), R6/1 mice and control mice (CTRL) (B) (D), zQ175 mice and control mice (CTRL) (E). The bar graphs show the mean t SEM.

Next, the invention will be illustrated by means of assays carried out by the inventors, that demonstrate the effectiveness of the product of the invention.

Materials and Methods

Human Tissue Samples

Brain samples from subjects suffering from HD and from healthy controls were provided by the Brain Bank Institute of Neuropathology (HUBICO-IDIBELL, Hospitalet de Llobregat, Spain), the Cien Foundation Tissue Bank (BT-CIEN, Madrid, Spain) and the Netherlands Brain Bank (Amsterdam, Netherlands). Written informed consent for post-mortem brain removal for diagnostic and research purposes was obtained from brain donors and/or close relatives. The blood samples and cerebrospinal fluid were provided by the Ramón y Cajal University Hospital Biobank after the informed consent of the study subjects.

Mice

Two mouse models were used: (1) R6/1 mice expressing human exon-1-Htt as a transgene and having a B6CBAF1 genetic background (Mangiarini et al., Cell. 1996; 87(3): 493-506) and (2) zQ175 mice with knock-in heterozygotes with an expanded CAG track in exon 1 of the Htt gene and having a C57BL/6J genetic background (Menalled et al., PLoS One. 2012; 7(12):e49838). Non-transgenic littermates (B6CBAF1 for R6/1 and C57BL/6J for zQ175) were used as control animals (CTRL) or wild-type animals (WT). The mice were housed with mixed genotypes in a number of four per cage and with food and water available ad libitum. They were kept in a temperature controlled environment on a 12/12 h light/dark cycle with light onset at 08:00. All mice were kept in the animal facility of the Severo Ochoa Molecular Biology Centre (CBMSO). The animal housing and maintenance protocols followed the guidelines of local authorities. The experiments with animals were carried out under the protocols (P15/P16/P18/P22) approved by the Institutional Animal Care and Use Committee of the Severo Ochoa Molecular Biology Centre (CBM Ethics Committee on Animal Experimentation, CEEA-CBM) and Community of Madrid PROEX 293/15.

The thiamine and/or biotin-based treatment was administered orally in the drinking water, with mice having normal drinking water as the treatment control and non-transgenic littermates as the genotype control.

In the case of R6/1 mice, treatment began at 3 weeks of age, just after weaning. The treatment with biotin consisted of a dose of 10 mg/kg/day, the treatment with thiamine started at a dose of 200 mg/kg/day and was decreased to 50 mg/kg/day after 18 weeks, and the combined treatment with thiamine and biotin consisted of a dose of 5 mg/kg/day of biotin+100 mg/kg/day of thiamine, which was reduced to 25 mg/kg/day at the age of 18 weeks. The different treatments were maintained until euthanasia, by cervical dislocation, at the age of 7-8 months, the treatment therefore having a total duration of approximately 32 weeks. The reason for lowering the thiamine dose after week 18 is that in a pilot group of mice in which the dose was not reduced, potential toxicity was detected in R6/1 mice starting at 24 weeks of age, evidenced by an increase in the volume of drink consumed and urination. These effects were no longer observed when the concentration of thiamine was reduced to a quarter of the initial concentration starting at 18 weeks of treatment.

In the case of zQ175 mice, the combined treatment with thiamine and biotin consisted of a dose of 5 mg/kg/day of biotin+100 mg/kg/day of thiamine with a duration of 3 to 6 months until euthanasia, by cervical dislocation, at the age of 7 months.

In all cases, the number of animals included in each group is mentioned in each example.

Gene Ontology Analysis

Co-immunoprecipitated CPEB4 mRNAs from RWP-1 cells based on the tables published in Ortiz-Zapater et al. (Nat Med. 2011; 18(1):83-90) and transcripts with changes in the poly(A) tail length (see section "PolyU Chromatography") were analysed in the striatum of symptomatic R6/1 mice (with an increase expressed in the number of times the initial value, "fold change" or "fc" 5-2 or a 2) with DAVID Bioinformatics Resources 6.7 (Laboratory of Immunopathogenesis and Bioinformatics; LIB) using the KEGG pathway annotation (Huang da et al., Nucleic Acids Res. 2009:37(1): 1-13).

Sequence Analysis of Cytoplasmic Polyadenylation Elements (CPE)

CPEs are the best characterised elements that regulate the cytoplasmic polyadenylation of mRNAs. The 3'UTR (untranslated region) sequences of the gene sets whose poly(A) is shortened, elongated or unaltered in R6/1 mice (based on "fc"≤−1.5 or ≥1.5) were extracted from Ensembl (www.ensembl.org/) and the incidence of canonical and functional CPEs was detected using the algorithm described in Pique et al. (Cell. 2008; 132(3):434-48) (genome.crg.es/CPE/).

Western Blot

Human brain samples were stored at −80° C. and ground with a mortar in a frozen environment with liquid nitrogen to prevent thawing of the samples, resulting in tissue dust. Mouse brain samples were quickly dissected after death on an ice plate and the different structures were stored at −80° C.

Human and mouse brain extracts were prepared by homogenising the brain samples in an ice-cold extraction buffer (20 mM HEPES, pH 7.4, 100 mM NaCl, 20 mM NaF, 1% Triton X-100, 1 mM sodium orthovanadate, 1 μM okadaic acid, 5 mM sodium pyrophosphate, 30 mM β-glycerophosphate, 5 mM EDTA, protease inhibitors (Complete, Roche, Cat. No. 11697498001)). The homogenates were centrifuged at 15,000 g for 15 min at 4° C. The resulting supernatant was collected and the protein content was determined by the Bradford assay using the Quick Start kit (Bio-Rad, 500-0203). 10 and 20 μg of total protein were subjected to 10% SDS-polyacrylamide gel electrophoresis, transferred to a nitrocellulose membrane (Amersham Protran 0.45 μm, GE Healthcare Life Sciences, 10600002) and blocked in TBS-T (150 mM NaCl, 20 mM Tris-HCl, pH 7.5, 0.1% Tween 20, supplemented with 5% powdered skim milk). The membranes were incubated overnight at 4° C. with the primary antibody in TBS-T supplemented with 5% powered skim milk, washed with TBS-T and then incubated with the corresponding secondary antibody, being revealed using the ECL detection kit (PerkinElmer, NEL105001EA). The images were scanned with a densitometer (Blo-Rad, GS-900) and quantified with Image Lab 5.2 (Bio-Rad).

The following rabbit-generated primary antibodies were used: CPEB1 (1:350, Santacruz, sc-33193); CPEB2 (1:1000, Abcam, ab51069); CPEB3 (1:1000, Abcam, ab10883); CPEB4 (1:1000, Abcam, ab83009); AUTS2 (1:750, Sigma, HPA000390); KTN1 (1:1000, Proteintech, Cat. 19841-1-AP); ROCK1 (1:1000, Abcam, ab45171); SLC19A3 (1:1000, Sigma, HPA038898); vinculin (1:1000, Abcam, ab129002); as well as mouse-generated anti-β-actin (1:25000, Sigma, A2228).

The secondary antibodies used were: HRP-conjugated anti-rabbit or anti-mouse IgG (1:2000, DAKO, P0447 for mice and P0448 for rabbits).

Poly(U) Chromatography

After euthanasia of the control WT and R6/1 mice (n=4) by cervical dislocation at the age of 7-8 months, the striatum was quickly dissected on an ice-cold plate and immersed in ice-cold RNAlater (Sigma, R0901). Next, the *striata* were homogenised and total RNA was purified with Ultraspec (Biotecx, BL-10050), frozen and stored at −80° C. until use.

The poly(A) RNA fraction was purified by poly(U) chromatography. Poly(U)-agarose (Sigma, p8563) was dissolved in 35 ml/g of expansion buffer (0.05 M Tris-HCl, pH 7.5, 1 M NaCl), incubated overnight at room temperature and loaded onto the chromatography column. An aliquot of total RNA was stored at −80° C. ("Input") and the rest was incubated with sample buffer (0.01 M Tris-HCl, pH 7.5, 1 mM EDTA, 1% SDS) for 5 min at 65° C. and subsequently cooled on ice. Next, binding buffer (0.05 M Tris-HCl, pH 7.5; 0.7 M NaCl; 10 mM EDTA; 25% [v/v] formamide) was added and the sample was loaded onto the poly(U)-agarose chromatography column (Mobitec, M1002s) and incubated for 30 minutes at room temperature (25° C.) under stirring. Subsequently, the column was washed three times at 25° C. and six times at 55° C. with wash buffer (0.05 M Tris-HCl, pH 7.5, 0.1 M NaCl, 10 mM EDTA, 25% [v/v] formamide). The washes carried out at 55° C. were collected and stored at −80° C. ("WASH" or "short poly(A) tail fraction"). The remaining poly(A) RNA ("ELUTED" or "long poly(A) tail fraction") was eluted with elution buffer (0.05 M HEPES, pH 7, 10 mM EDTA, 90% [v/v] formamide) at 55° C. and stored at −80° C.

The RNA of the two poly(A) fractions, the short poly(A) tail fraction and the long poly(A) tail fraction, was precipitated by adding 1 volume of isopropanol, 1/10 volume of 3 M sodium acetate pH 5.2 and 20 μg of glycogen (Sigma, G1767). The samples were incubated at −20° C. for 20 min and centrifuged for 15 min at 14,000 g at 4° C. The supernatant was removed and the precipitate was washed with 750 μl of ethanol and centrifuged at 14,000 g and 4° C. for 5 min. The supernatant was removed and the precipitate was air dried for 5 min. The RNAs were resuspended in 300 μl of nuclease-free water and 300 μl of acid phenol:chloroform (5:1) were added. The samples were vortexed and centrifuged for 10 minutes at 14,000 g and 4° C.

RNA quantification was performed using the Qubit fluorometer using the Qubit RNA Hs assay kit (Thermo-Fisher Scientific, 032852). RNA integrity quality control was performed with the Agilent Bioanalyzer 2100, using the RNA Nano Assay (Agilent Technologies 5067-1511) and the RNA Pico Assay (Agilent Technologies 5067-1513).

The preparation of the cDNA library and its amplification was carried out with the WTA2 kit using a template of 2 to 5 ng of total RNA and following the manufacturer's instructions (Sigma-Aldrich). The cDNA was amplified for 22 cycles and purified using the PureLink Quick PCR purification kit (Invitrogen, K310001). The quantification of the amplified cDNA was performed in a Nanodrop ND-1000 (Thermo-Fisher Scientific), and 8 μg of the cDNA from each sample were fragmented and labelled using the GeneChip Mapping 250K Nsp assay kit (Affymetrix, 900753) following the manufacturer's instructions.

Hybridisation was performed using the GeneAtlas Hyb, Wash and Stain kit for 3' IVT arrays. The samples ready for hybridisation were denatured at 96° C. for 10 minutes before incubation on a MG-430 PM mouse array (Affymetrix, 901570) and hybridisation was performed for 16 hours at 45° C. in the GeneAtlas hybridisation oven (Affymetrix, 00-0331). After said time has lapsed, washing and staining were carried out in the GeneAtlas Fluidics Station (Affymetrix, 00-0079), following the specific script for MG-430 PM mouse arrays. Lastly, the arrays were scanned with the GeneAtlas Scanner (Affymetrix) using predefined parameters, and CEL files for bioinformatic analysis were generated with the GeneAtlas software (Affymetrix).

Array processing was performed using R (R Development Core Team. R: A language and environment for statistical computing, R Foundation for Statistical Computing, 2014) and Bioconductor (Gentleman et al., Genome Biol. 2004; 5, R80). The raw CEL files were normalised using RMA background correction and the abstract was generated as indicated in Irizarry R A. et al. (Stat Appl Genet Mol Biol. 2003; 2:Article1). Standard quality controls were performed to identify abnormal samples, as indicated in Gentleman R. et al, 2005 (Springer, New York) with respect to: (a) spatial artifacts in the hybridisation process (scanning images and pseudo-images of probe level models); (b) intensities dependent on the differences between chips (MvA plots); (c) RNA quality (RNA digestion plot); and (d) overall intensity levels (box plot of perfect match log-intensity distributions before and after normalisation and RLE plots). Probe annotation was performed using the information available on the Affymetrix website (www.affymetrix.com/analysis/index.affx) using the na35 version.

The expression values were adjusted for technical bias as described in Eklund and Szallasi (Genome Biol. 2008; 9, R26) using a linear model and implemented with the "limma" R package (Ritchie et al., Nucleic Acids Res. 2015; 43, e47). For each biological replica, the change in the log 2 value was calculated between the "WASH" and "ELUTED" samples and was used to find significant differences between control WT and R6/1 mice. The differential expression was performed using a linear model with fluidic mechanisms and amplification batches as covariates. "Fold change" values ≤−1.5 in at least one probe mean that the poly(A) tail is shortened in the transcript of said gene in R6/1 mice, ≥1.5 in at least one probe means that it is elongated, and intermediate values mean there is no change. If the same transcript showed opposite results for different probes, it was considered to be unchanged.

Quantitative Real-Time PCR

Quantification was performed by real-time PCR using a CFX 384 Real Time System C1000 thermal cycler (Bio-Rad) in combination with SsoFast Eva Green (Blo-Rad, CN 172-5204) and 0.25 μM of each oligonucleotide primer pair was used. The data was analysed by GenEx 5.3.7 software (MultiD Analyses AB). mRNA levels were normalised first with respect to total RNA and then with respect to the expression of the following genes: 18S ribosomal subunit, β-Actin, GAPDH and β-Tubulin.

TABLE 2

| Human primers | | | |
|---|---|---|---|
| CPEB1 | Forward | 5'-ggcagccatcttgaacga-3' | SEQ ID NO: 1 |
| | Reverse | 5'-aagtcacacgaccagaacca-3' | SEQ ID NO: 2 |
| CPEB2 | Forward | 5'-gcctcataaagcagaaagcaa-3' | SEQ ID NO: 3 |
| | Reverse | 5'-agcatcaatgagtgcctgaa-3' | SEQ ID NO: 4 |
| CPEB3 | Forward | 5'-gaacgctactctagaaaggtgtttg-3' | SEQ ID NO: 5 |
| | Reverse | 5'-cgaaagctggcagtgatct-3' | SEQ ID NO: 6 |
| CPEB4 | Forward | 5'-cactgtttccaatggaagatgg-3' | SEQ ID NO: 7 |
| | Reverse | 5'-ggtgaacccaggccactatg-3' | SEQ ID NO: 8 |
| AUTS2 | Forward | 5'-gaagcggagagagtccacct-3' | SEQ ID NO: 9 |
| | Reverse | 5'-tcctgaggcttaagtgctacatc-3' | SEQ ID NO: 10 |
| ROCK1 | Forward | 5'-tcccctcgaacgctttctac-3' | SEQ ID NO: 11 |
| | Reverse | 5'-tgtatttttgaccactttccgga-3' | SEQ ID NO: 12 |
| KTN1 | Forward | 5'-atttcagaaagagagaaagaaataagtgg-3' | SEQ ID NO: 13 |
| | Reverse | 5'-tgttcaactgcatccttcaaaga-3' | SEQ ID NO: 14 |
| SLC19A3 | Forward | 5'-agttcctggatttaccccactg-3' | SEQ ID NO: 15 |
| | Reverse | 5'-ggttctgagggtctcatcatgg-3' | SEQ ID NO: 16 |
| 18S | Forward | 5'-atccattggagggcaagtc-3' | SEQ ID NO: 17 |
| | Reverse | 5'-gctcccaagatccaactacg-3' | SEQ ID NO: 18 |
| β-TUBULIN | Forward | 5'-ctttgtggaatggatcccca-3' | SEQ ID NO: 19 |
| | Reverse | 5'-gactgccatcttgaggcca-3' | SEQ ID NO: 20 |

For the amplification of the GAPDH (qA-01-0101S) and β-ACTIN (qA-01-0104S) genes, commercial primers obtained from TATAA Biocenter (Vestec, Czech Republic) were used.

TABLE 3

| Mouse primers. | | | |
|---|---|---|---|
| Cpeb1 | Forward | 5'-ttatctgcagctcacaacctg-3' | SEQ ID NO: 21 |
| | Reverse | 5'-gcaaaagtacttgaagcagacct-3' | SEQ ID NO: 22 |
| Cpeb2 | Forward | 5'-ctgcagcagaggaactcgta-3' | SEQ ID NO: 23 |
| | Reverse | 5'-ggttgctccaaggagactgt-3' | SEQ ID NO: 24 |
| Cpeb3 | Forward | 5'-aaaacccagccccagtct-3' | SEQ ID NO: 25 |
| | Reverse | 5'-gcttggggatctctgagga-3' | SEQ ID NO: 26 |
| Cpeb4 | Forward | 5'-caaatcttattttccaccaaaagg-3' | SEQ ID NO: 27 |
| | Reverse | 5'-catcaatgagagcctgaacaga-3' | SEQ ID NO: 28 |
| Auts2 | Forward | 5'-cctccaggccctagtctctt-3' | SEQ ID NO: 29 |
| | Reverse | 5'-aaggggtcccagtaggatgt-3' | SEQ ID NO: 30 |
| Rock1 | Forward | 5'-gatcccaaatcggaagtgaa-3' | SEQ ID NO: 31 |
| | Reverse | 5'-tcataaaccagggcatcca-3' | SEQ ID NO: 32 |
| Ktn1 | Forward | 5'-ttaaaagctgaagtgcagaaattg-3' | SEQ ID NO: 33 |
| | Reverse | 5'-acctcatgtgcggtagcag-3' | SEQ ID NO: 34 |
| Slc19a3 | Forward | 5'-gagcagtagaggccatagcaa-3' | SEQ ID NO: 35 |
| | Reverse | 5'-ccttcagatagcccactgaga-3' | SEQ ID NO: 36 |
| 18s | Forward | 5'-ctcaacacgggaaacctcac-3' | SEQ ID NO: 37 |
| | Reverse | 5'-cgctccaccaactaagaacg-3' | SEQ ID NO: 38 |
| Gapdh | Forward | 5'-ctcccactcttccaccttcg-3' | SEQ ID NO: 39 |
| | Reverse | 5'-cataccaggaaatgagcttgacaa-3' | SEQ ID NO: 40 |
| β-Actin | Forward | 5'-ctaaggccaaccgtgaaaag-3' | SEQ ID NO: 41 |
| | Reverse | 5'-accagaggcatacagggaca-3' | SEQ ID NO: 42 |
| β-Tubulin | Forward | 5'-gacctatcatggggacagtga-3' | SEQ ID NO: 43 |
| | Reverse | 5'-cggctctgggaacatagttt-3' | SEQ ID NO: 44 |

Immunohistochemistry

Human brain samples (cortex and striatum) were fixed with formalin (4%, 24 h), and embedded in paraffin. The sections (5 μm thick) were mounted on superfrost-plus tissue slides and deparaffinised. Peroxidase activity was stopped with 0.3% $H_2O_2$ in methanol for 30 minutes, followed by epitope unmasking with 10 mM citrate buffer pH 6.0 microwaved for 15 minutes.

The sections were immersed for 1 hour in blocking solution (PBS supplemented with 0.5% foetal bovine serum, 0.3% Triton X-100 and 1% BSA) and incubated overnight at 4° C. with rabbit-generated anti-SLC19A3 antibody (Sigma, HPA038898) diluted 1:1000 in blocking solution. After washing, they were incubated with biotinylated anti-rabbit secondary antibody and then with the avidin-biotin complex using the Elite Vectastain kit (Vector Laboratories, PK-6101). Chromogen reactions were performed with diaminobenzidine (SIGMAFAST DAB, Sigma, D4293) for 10 minutes and then the sections were dehydrated and covered with DePeX (Serva). Images were captured using an Olympus BX41 microscope with an Olympus DP-70 camera (Olympus Danmark A/S).

Thiamine Detection

Cerebrospinal fluid (CSF), blood and striatal homogenate samples from both humans and mice were collected in a vial protected from light and stored at −80° C. For the striatal samples, the frozen tissue was homogenised and the protein content was determined by the Bradford assay using the Quick Start kit (Bio-Rad, 500-0203).

For the human, blood and mouse striatum samples, 100 μl of extraction buffer (Chromsystems, 37003) were added to 100 μl of sample and mixed for 2 s under stirring. Next, 150 μl of precipitation reagent (Chromsystems, 37004) were added and mixed again for 30 s under stirring. Subsequently, they were centrifuged for 5 min at 10,000 g and a 100 μl derivatisation mixture (Chromsystems, 37005-6) was selected in a new reaction vial to which 50 μl of the sample supernatant was added to briefly mix again. Then, 50 μl of neutralisation buffer (Chromsystems, 37009) and 50 μl of stabilisation buffer (Chromsystems, 37007) were added and it was left to rest for 20 minutes.

For mouse CSFs, the cisterna magna was directly extracted through capillaries. 2 μl of CSF were diluted in 7 μl of physiological saline. The previously described protocol was scaled up for a sample volume of 9 instead of 100 μl of sample.

Next, 50 μl were injected into the HPLC system. A common chromatographic method for the analysis of thiamine derivatives (TPP, TMP and free thiamine) was standardised. Lastly, the percentages of each thiamine derivative were calculated from the data in nmol/g of protein for the striatal samples, whereas the amount of each thiamine derivative was calculated as nmol/L for total blood and CSF.

Open Field

Locomotor activity analysis was performed in 27.5 cm×27.5 cm transparent Plexiglas® boxes equipped with photoelectric detectors to monitor horizontal and vertical activity. Activity levels were recorded with a MED Associates activity monitor (MED Associates, St. Albans, VT) and analysed with MED Associates activity monitor data analysis software v.5.93.773. Control WT or R6/1 mice were placed in the centre of the open field box and allowed to move freely. Data was recorded individually for each animal for 15 min and the distance covered by the animal was measured.

Rotarod

Motor coordination analysis was analysed at 18 weeks in R6/1 mice in a rotarod acceleration apparatus (Ugo Basile). The mice were trained beforehand for two days: Day 1: 4 rpm for 1 minute, four repetitions; Day 2: acceleration from 4 to 8 rpm for 1 minute followed by constant 8 rpm for 1 minute, four repetitions. On the third day, the test was performed with the rotarod apparatus set to accelerate from 4 to 40 rpm for 5 min, four repetitions, and the time it took for the mouse to fall from the bar was measured.

Magnetic Resonance T2

The animals were placed in the centre of the RF (radiofrequency) volume coil and positioned on the magnet under continuous inhalation anaesthesia through a nasal mask. A respiratory sensor connected to a monitoring system (SA Instruments, Stony Brook, NY) was placed under the abdomen to monitor the rate and depth of respiration. The mice were anaesthetised with 2% isoflurane in 1 L oxygen in an induction chamber and the anaesthetic gas flow was constantly regulated to maintain a respiratory rate of 50+/−20 ppm. The temperature of the animals was maintained at approximately 37° C. by passing hot water through a heat exchanger to the animal platform. The physiological status of the animals was monitored using an NMR-compatible small animal gating system by SA Instruments (Stony Brook, NY; www.i4sa.com/) which controlled the respiratory rate.

NMR experiments were performed on a Bruker Pharmascan system (Bruker Medical Gmbh, Ettlingen, Germany) using a 7.0-T superconducting magnet with a horizontal diameter, equipped with a 23 mm selective cage resonator $^1H$ and a 90 mm-diameter Bruker gradient insert (maximum intensity 36 G/cm). All data was acquired using a Hewlett-Packard dashboard with Paravision 5.1 software (Bruker Medical Gmbh) operating on a Linux platform.

The T2-weighted (T2-W) spin-echo images were taken with a rapid acquisition with relaxation enhancement (RARE) sequence in axial orientations and the following parameters: TR=3000 ms, TE=14.7 ms, RARE factor=8, Av=6, FOV=2.3 cm, acquisition matrix=256×256, slice thickness=1.00 mm without gap and number of slices=16.

Diffusion Tensor (DTI)

Diffusion tensor data was obtained with a sequence of spin-echo pulses, single shot and planar imaging (EPI) using the following parameters: TR/TE 3500/40 ms; an average signal of 4.7 non-collinear diffusion gradient schemes with a diffusion weighting of b=100 and 1400 s/mm2, 1 mm thick slices without gap, field of view 23×23 mm and acquisition matrix=128×128.

Fractional anisotropy, mean diffusivity, layout, eigenvalues and eigenvector maps were calculated with an in-house software application written in Matlab (R2007a).

Magnetic Resonance Spectroscopy

The nuclear magnetic resonance (NMR) spectroscopy study $^1H$ was performed in the striatal region of the right hemisphere. The in vivo spectroscopy protocol used Point Resolved Spatial Spectroscopy (PRESS), combined with VAPOR water suppression, and the following parameters were used: TR=3000 ms, TE=35 ms, Av=128, voxel volume=3 mm3. Before acquisition, the FASTMAP automatic shimming procedure (Gruetter, R. Magn. Reson. Med. 1993; 29: 804-811) is used to achieve optimal uniformity of the magnetic field across the voxel volume. All spectra of $^1H$ were automatically analysed using LC Model version 6.2 OR (Stephen Provencher, Oakville, ON; Canada).

Statistical Analysis

Statistical analysis was performed with SPSS 21.0 (SPSS® Statistical IBM®). The data is represented as mean±SEM (standard error of the mean) with a 95% confidence interval.

Data normality was analysed using the Shapiro-Wilk test (n<50) or Kolmogorov-Smimov test (n>50). Homogeneity of variance was analysed using Levene's test.

To compare two independent groups of the unpaired Student's t-test (data with normal distribution), Mann-Whitney-Wilcoxon or Kolmogorov-Smirnov tests (with non-normal distribution) were performed. To compare the dependent measurements, a paired t-test (normal distribution) or Wilcoxon signed-rank tests (non-normal distribution) were used. For multiple comparisons, data with a normal distribution was analysed using a one-way ANOVA test followed by Tukey's post hoc test, Games-Howell test or Dunnett's T test. Statistical significance of non-parametric data for multiple comparisons was determined using the Kruskal-Wallis one-way ANOVA test. Enrichment tests were performed using the one-sided Fisher's exact test. A critical value for significance of $p<0.05$ was used throughout the study.

Results

Example 1. CPEB1 and CPEB4 Protein Levels are Altered in Huntington's Disease

Figure 1B:
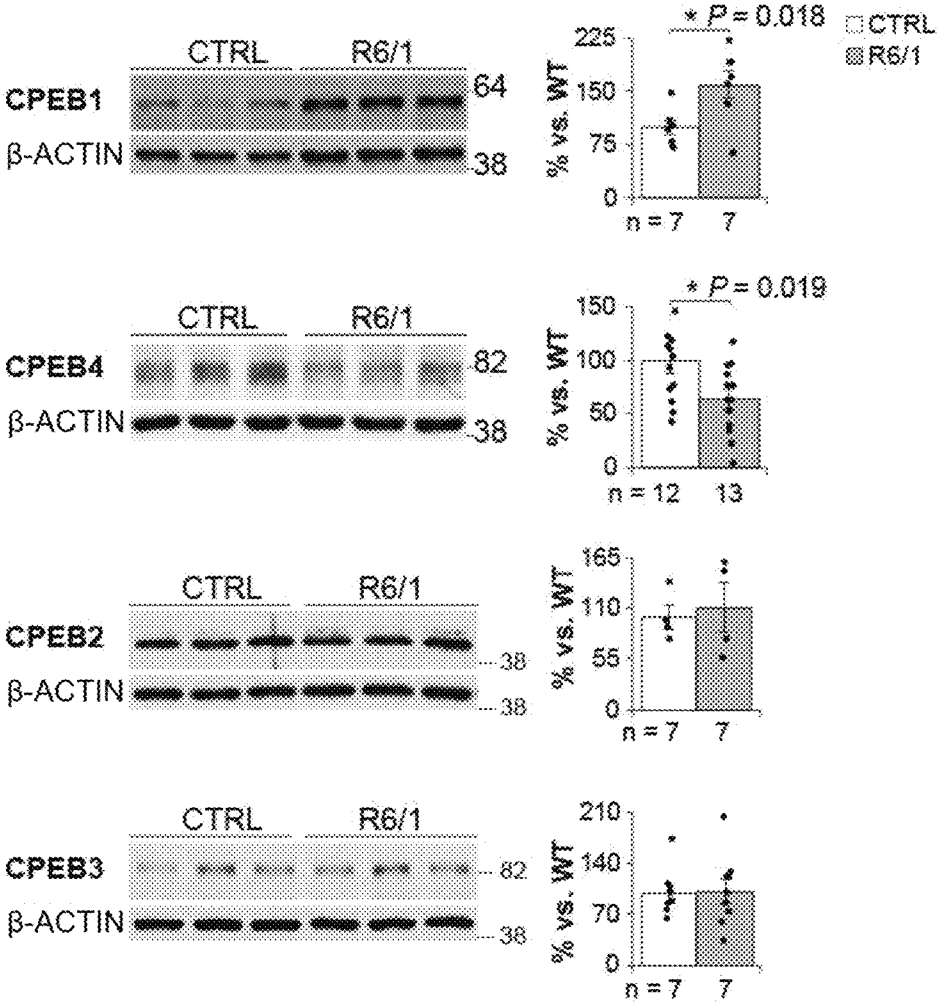

A statistically significant increase in the CPEB1 protein levels (453%, p=0.037) and a statistically significant decrease in CPEB4 (83% decrease, p=0.001) were found in the post-mortem striatum of subjects with HD; no significant changes were found in the levels of CPEB2 or CPEB3 (FIG. 1A). Equivalent results were found in the striatum of the R611 transgenic mouse model (FIG. 1B).

Figure 1C:
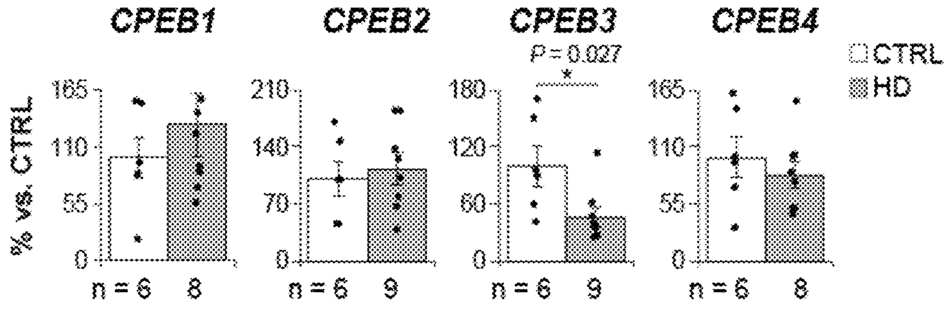
Figure 1D:
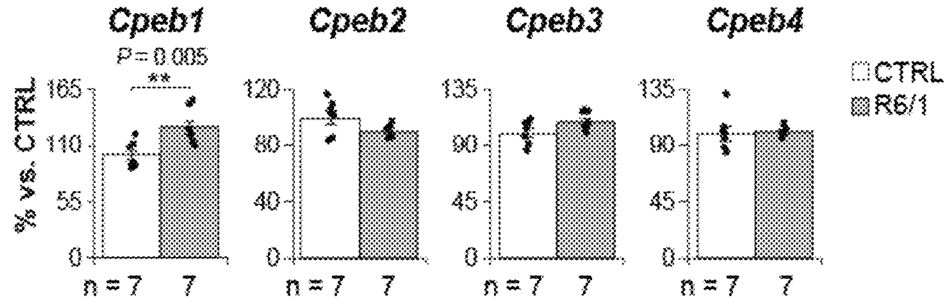

In general, the CPEB1/CPEB4 imbalance at the protein level did not correlate with corresponding alterations in transcript levels (FIG. 1C-D), except for increased CPEB1 mRNA levels in the striatum of R6/1 mice (FIG. 1C).

Figure 1E:

In zQ175 knock-in mice, the mouse model of slow disease progression, only the decrease in CPEB4 levels reached statistical significance (FIG. 1E), suggesting that changes in CPEB4 might precede changes in CPEB1.

Example 2. Analysis of the Polyadenylation of Gene Associated with Huntington's Disease To detect possible changes in the length of the poly(A) tail in the transcriptome of R6/1 mice with respect to control mice, poly(U) column chromatography was performed and followed by a gene chip analysis.

Figure 2A:
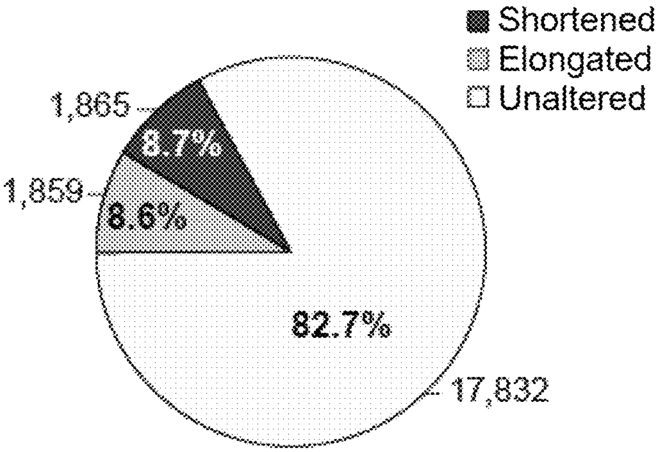
FIG. 2 shows Poly(U) chromatography. (A) Percentage of genes whose transcripts have shortened, elongated or unaltered poly(A) tails in the striatum (St) of R6/1 mice. (B) Gene ontology analysis of mRNAs with changes in their poly(A) tail in St of R6/1. (C) Venn diagram of transcripts with altered poly(A) involved in neurodegenerative diseases. (D) Percentage of transcripts with CPE sequences in their 3' UTR as a function of their poly(A) tail status in R6/1 mice.

The results revealed that in the striatum of R6/1 mice the length of the poly(A) tail is longer in the transcripts of 8.6% of the genome and shorter in those of 8.7% (FIG. 2A).

Figure 2B:
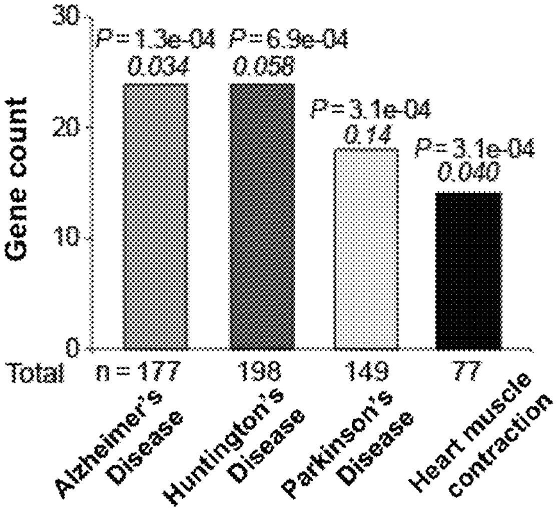
Figure 2C:
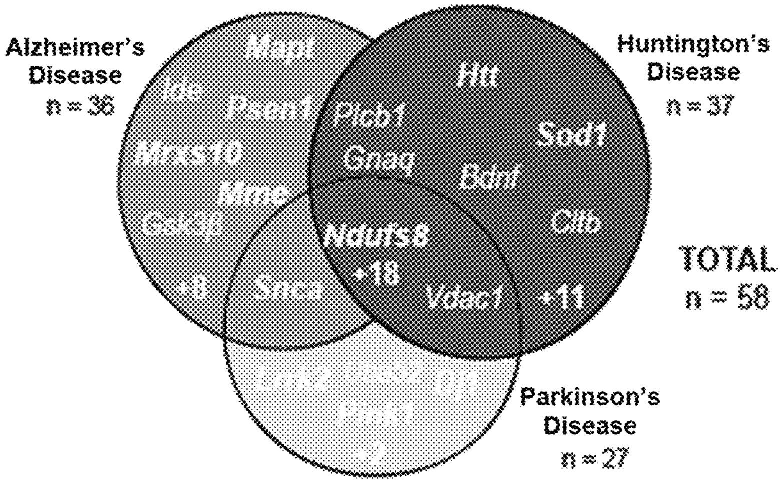

Subsequently, the gene ontology analysis (KEGG Pathway) on 1,467 genes with an absolute change of poly(A) (f.c.; fold change) above 2 (FIG. 2B) produced four terms with Benjamini <1.5e-1; among them: HD, Alzheimer's disease (AD), Parkinson's disease (PD) and heart muscle contraction. Thus, these results indicate that altered polyadenylation may contribute to pathogenesis not only in HD, but also in other neurodegenerative pathologies, such as AD and PD, since many of the genes mutated in familial forms of AD/tauopathies, PD or amyotrophic lateral sclerosis, such as the Psin1, Mapt, Snca, LrrK2, Pink1, Dj1 and Sod1 genes, along with the Htt gene, showed altered polyadenylation (FIG. 2C).

Figure 2D:
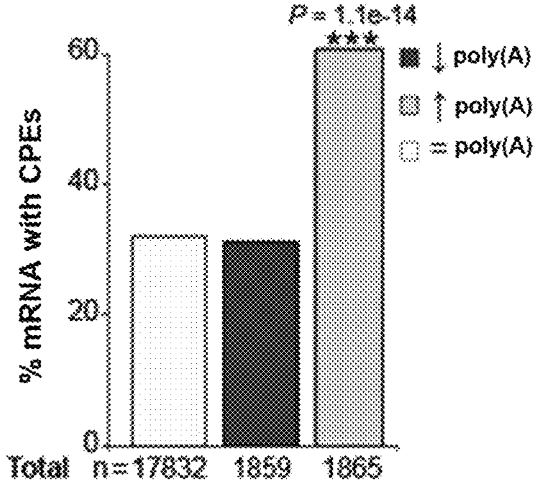

To corroborate that the observed changes in polyadenylation could be attributed to an altered function of the CPEB proteins, the potential enrichment of genes with CPE sequences in their 3'UTRs was analysed. In fact, this was the case for transcripts with the shortened poly(A) tail (FIG. 2D). Moreover, 93% of the genes with the most extreme shortening (f.c.<−4.0) of their poly(A) tail have CPE sequences in their 3'UTRs (Table 4).

TABLE 4

Genes with greater shortening (f.c. < −4.0) of their poly(A) tail.

| Fold-change | Symbol | Name of the gene | No. of CPEs |
|---|---|---|---|
| −5.4 | Auts2 | Autism susceptibility candidate 2 | 2 |
| −5.3 | Akap10 | A kinase (PRKA) anchor protein 10 | 1 |
| −5.0 | Zfp518a | Zinc finger protein 518A | 5 |
| −5.0 | Tcf12 | Transcription factor 12 | 2 |
| −4.9 | Zw10 | Zw10 kinetochore protein | 0 |
| −4.9 | Rock1 | Rho-associated coiled-coil containing protein kinase 1 | 4 |
| −4.9 | Spcs1 | Signal peptidase complex subunit 1 | 2 |
| −4.7 | Lax1 | Lymphocyte transmembrane adapter 1 | 1 |
| −4.6 | Memo1 | Mediator of cell motility 1 | 2 |
| −4.5 | Ktn1 | Kinectin 1 | 3 |
| −4.3 | Tfrc | Transferrin receptor | 2 |
| −4.2 | Nmd3 | NMD3 homolog (*S. cerevisiae*) | 3 |
| −4.1 | Slc19a3 | Solute carrier family 19, members | 3 |

Figure 3A:
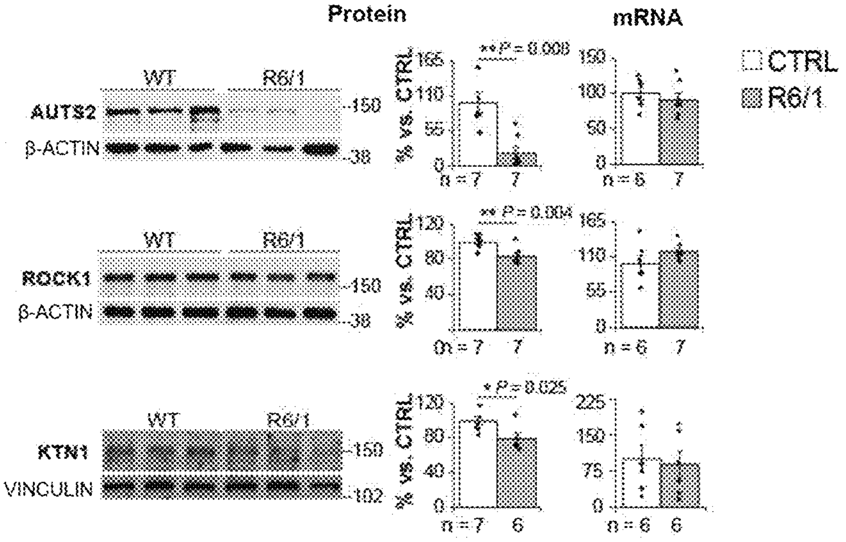
FIG. 3 shows protein and mRNA levels of proteins and genes showing poly(A) tail shortening in R6/1 mice. Western blot of AUTS2, ROCK1 and KTN1 proteins in the striatum of: (A) R6/1 mice and control mice (CTRL) and (B) subjects suffering from HD (HD) and control subjects (CTRL). To the right of each panel, the mRNA levels obtained by RT-PCR for each of the genes that encode for the mentioned proteins are also shown.
Figure 3B:
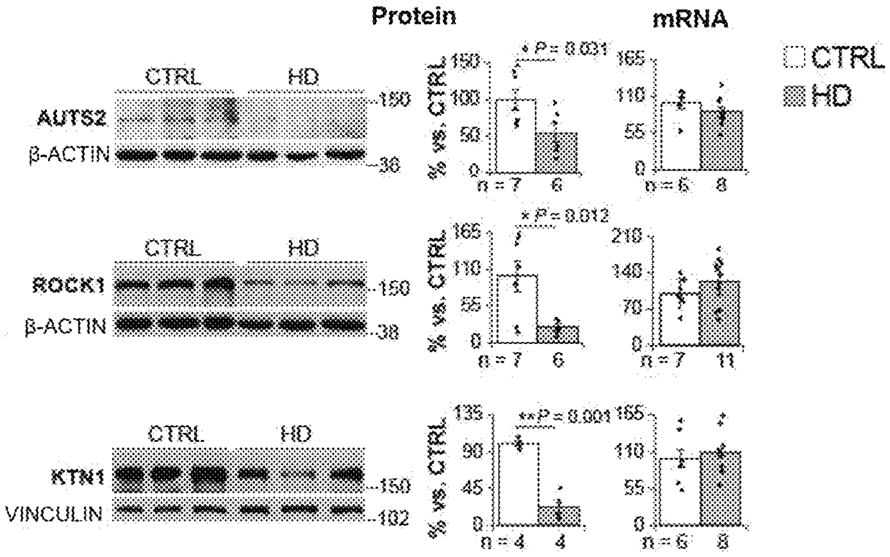

The decreased polyadenylation is expected to be reflected in protein levels that have also decreased. Thus, the results obtained confirm a great decrease in the levels of the Auts2 protein (the gene with the highest degree of deadenylation, f.c.=−5.4; Table 4) in both the striatal tissue of R6/1 mice (FIG. 3A) and in subjects suffering from HD (FIG. 3B), despite having an unaltered transcriptional level. Similar results were found for other genes with a deadenylation of f.c.<−4, such as the Rock1 and ktn1 genes (FIG. 3A-B and Table 4).

Therefore, the results shown indicate the existence of an imbalance between the CPEB1/CPEB4 protein levels in the striatum of subjects with HD and in the R6/1 mouse model of HD, as well as an overall alteration in the length of the poly(A) tail, which notably affects genes associated with neurodegeneration. Moreover, the enrichment of the CPE sequences in the genes showing deadenylation indicates that the latter could be secondary to the alteration of the CPEB proteins. Likewise, highly deadenylated genes show decreased protein levels in both the R6/1 mouse model of HD and in the striatum of subjects suffering from the pathology, in the absence of coincident changes in the transcript levels.

Example 3. Subjects with Huntington's Disease have a Decreased Concentration of the SLC19A3 Protein in the Brain and a Deficiency of Thiamine Levels Among the most prominently deadenylated genes shown in Table 4, the Slc9a3 gene was particularly interesting because its mutations cause a devastating basal ganglia disorder called biotin-thiamine-responsive basal ganglia disease that can be reversed with therapy based on the administration of said vitamins. More specifically, the Slc19a3 gene encodes a transmembrane thiamine transporter (hTHTR2) and subjects with this pathology show decreased thiamine levels in the cerebrospinal fluid, bilateral atrophy of the caudate nucleus in the head and in the putamen, as well as a variety of neurological symptoms, including lethargy, irritability, dystonia, spasticity, tremor and chorea, among others, which improve with a thiamine and biotin-based treatment. Thus, the inventors hypothesised that HD might be, in part, a thiamine deficiency due to decreased levels of the SLC19A3 protein.

To corroborate their hypothesis, the SLC19A3 protein concentration was then analysed in mouse and human brain samples.

Figure 4A:
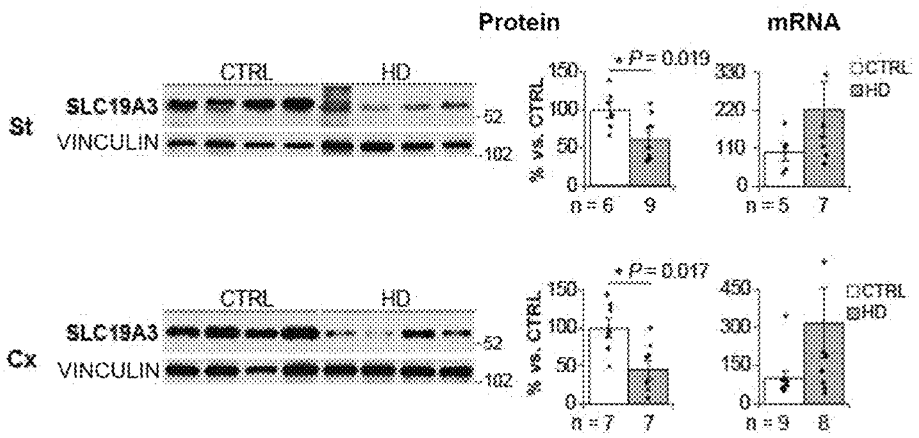
FIG. 4 shows an analysis of gene and protein expression of SLC19A3 and thiamine in subjects with HD. (A) Protein and mRNA levels of SLC19A3 in the striatum and cortex of subjects with HD (HD) and control subjects (CTRL). (B) Immunohistochemical photographs showing the immunolocalisation of SLC19A3 in striatal (St) and cortex (Cx) sections of subjects with HD (HD) and healthy control subjects (CTRL). (C) Concentration of thiamine pyrophosphate (TPP), thiamine monophosphate (TMP) and free thiamine, as well as the sum of the three (total) in cerebrospinal fluid (CSF) and total concentration of thiamine in the blood of healthy control subjects (CTRL) and subjects with HD (HD). (D) Percentage of thiamine forms: thiamine pyrophosphate (TPP), thiamine monophosphate (TMP) and free thiamine in striatum from healthy control subjects (CTRL) and subjects with HD. The bar graphs show the mean±SEM.
Figure 4B:
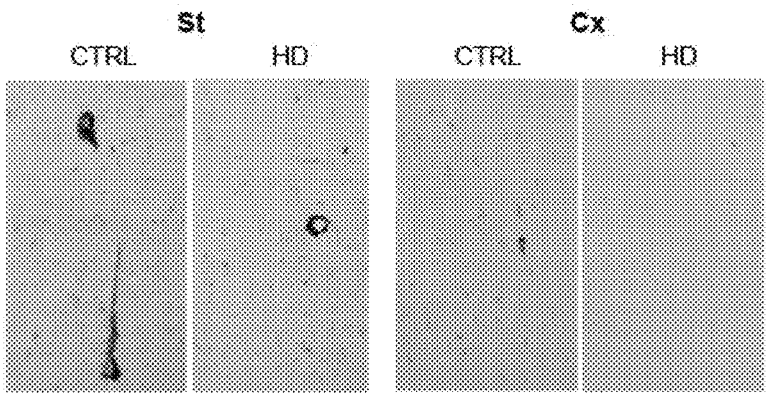
Figure 4C:
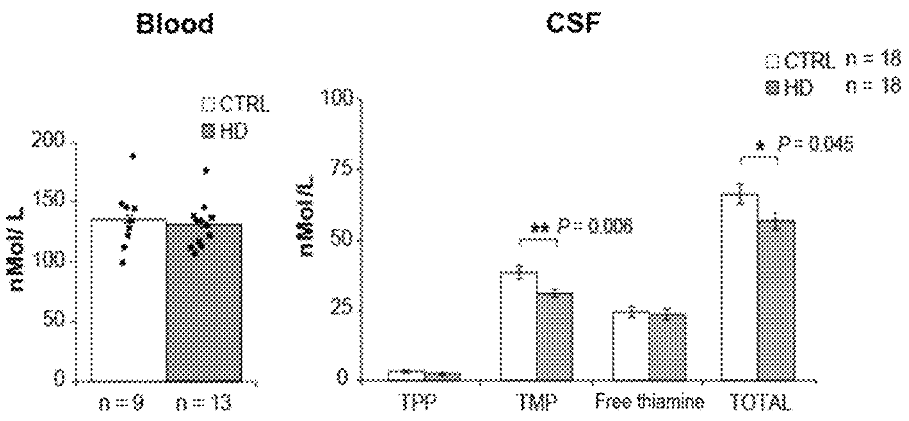

SLC19A3 protein levels were significantly lower in both the striatum and the cortex of subjects with HD, despite trending towards higher transcript levels (FIG. 4A). This is reflected in a significant decrease in immunohistochemical staining in both striatal and cortical histological samples (FIG. 4B) which, in good agreement with the human protein atlas (www.proteinatlas.org), revealed a neuronal and endothelial localisation. Moreover, decreased thiamine levels in the CSF of subjects with HD were also observed, although with unaltered blood levels (FIG. 4C). This is in line with the decrease of thiamine in CSF which was previously observed in subjects suffering from BTBGD (Ortigoza-Escobar, J. D., et al. Brain. 2016; 139:31-38).

Inside the cell, thiamine is converted to its phosphorylated derivatives, such as thiamine monophosphate (TMP) and, more importantly, thiamine triphosphate (TPP), which is the bioactive form that acts as a cofactor for multiple enzymes in the catabolism of sugars and amino acids. TPP accounts for 80-85% of the thiamine present in the brain. However, when the level of free thiamine and its phosphorylated derivatives was analysed in the striatal tissue of subjects with HD, the results showed that TPP represents only 60% of the sum of Free thiamine+TMP+TPP, with a corresponding increase in the percentage of free thiamine (FIG. 4D), which is indicative of a decrease in the intracellular availability of thiamine.

On the whole, these results demonstrate a decreased concentration of the SLC19A3 protein together with a deficiency of thiamine levels in the brain of subjects with HD, and they suggest that subjects suffering from this pathology could benefit from a thiamine and/or biotin-based therapy, as do subjects with BTBGD.

Figure 4D:
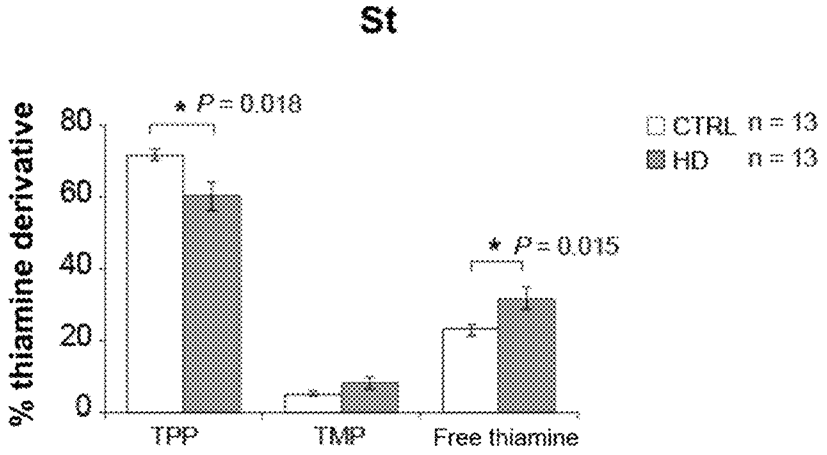
Figure 5A:
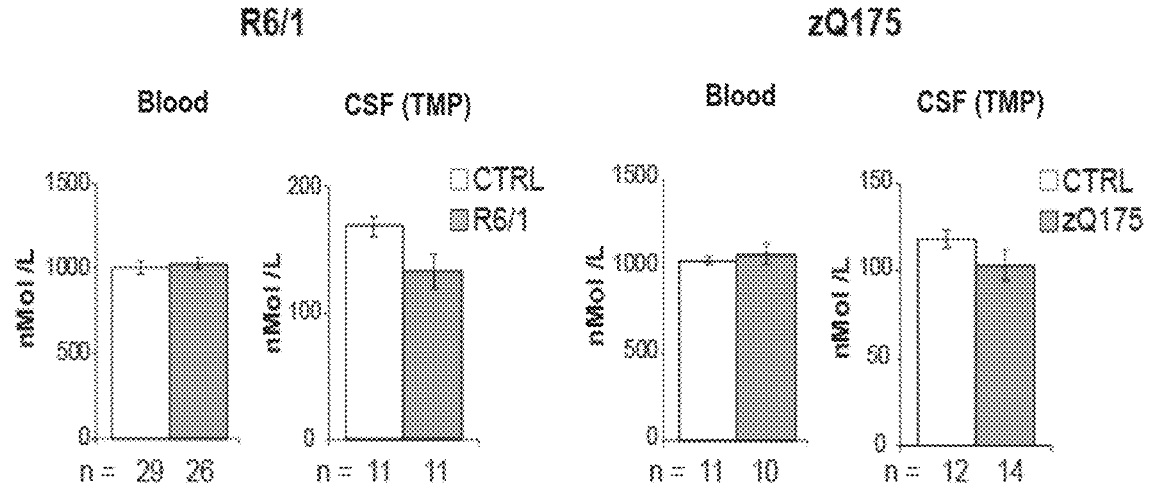
FIG. 5 shows thiamine levels in mouse models of HD. (A) Concentration of thiamine monophosphate (TMP) in cerebrospinal fluid (CSF) and total concentration of thiamine in the blood of control mice (CTRL) and R6/1 mice, and of control mice (CTRL) and zQ175 mice. (B) Percentage of thiamine forms: thiamine pyrophosphate (TPP), thiamine monophosphate (TMP) and free thiamine in striatum of control mice (CTRL) and R6/1 mice, and of control mice (CTRL) and zQ175 mice. The bar graphs show the mean±SEM.
Figure 5B:
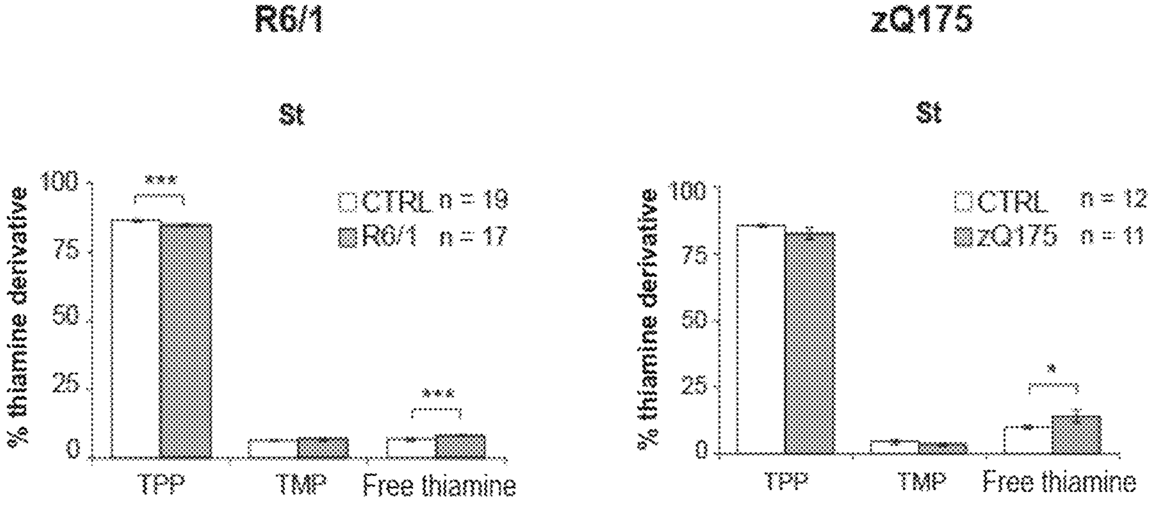

Example 4. The Combined Administration of Thiamine and Biotin in Mouse Models of HD Improves Motor Symptoms and Striatal Atrophy To preclinically test whether administering thiamine and biotin could be useful in the treatment of HD, an analysis was first performed to determine whether the tested mouse models of HD: R6/1 and zQ175, also had a thiamine deficiency, as has been shown in subjects suffering from HD. As observed in FIG. 5A, both mouse models showed unaltered blood thiamine levels and a trend towards lower TMP levels in CSF. The distribution of thiamine and its phosphorylated derivatives, TPP and TMP, in the striatal tissue of said mice versus control WT mice was also analysed, revealing an increase in free thiamine (FIG. 5B) in both models and a decrease in TPP in R6/1 mice (FIG. 5B) which also happens in the samples of subjects suffering from HD (FIGS. 4C and 4D, respectively).

Since R6/1 mice exhibit motor phenotypes from an early age, the decision was made to administer the treatment based on biotin (B), thiamine (T) or a combination of both (B+T) when they stopped breastfeeding (i.e., three weeks after the birth of the mice), and analyse the effect of each treatment on hypoactivity, observed in the open field test at 13 weeks of age, and on motor coordination deficit, detected in the rotarod test at 18 weeks of age.

Figure 6A:
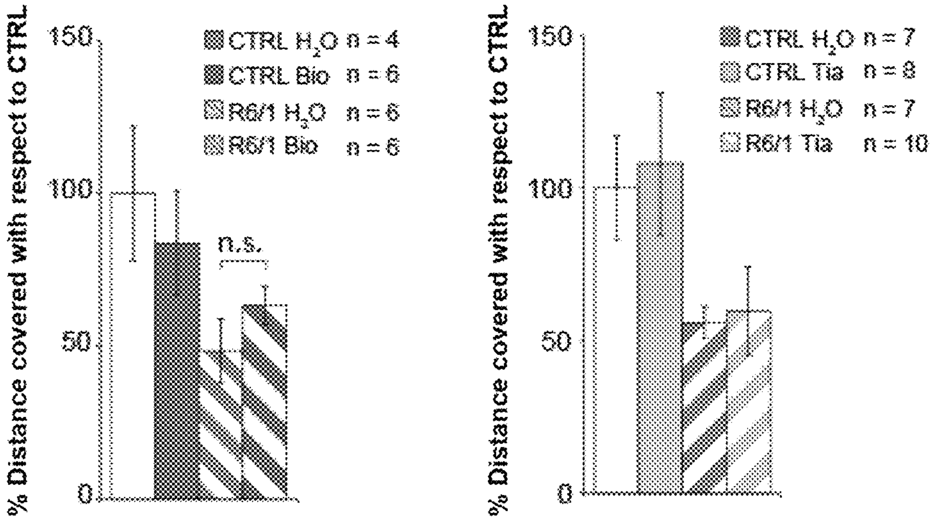
FIG. 6 shows a phenotypic analysis of R6/1 mice treated with thiamine, biotin or both. Percentage of (A) distance covered in the open field test at 13 weeks and (B) time it takes for the untreated R6/1 mice ($H_2O$) or the R6/1 mice treated with biotin (Bio) or thiamine (Tia) to fall in the Rotarod test at 18 weeks, with respect to the untreated WT mice ($H_2O$) or the WT mice treated with biotin (Bio) or thiamine (Tia). (C) Percentage of time it takes for the untreated R6/1 mice ($H_2O$) or the R6/1 mice treated with biotin and thiamine (B+T) to fall in the Rotarod test at 18 weeks, with respect to the untreated WT mice ($H_2O$) or the WT mice treated with biotin and thiamine (B+T).
Figure 6B:
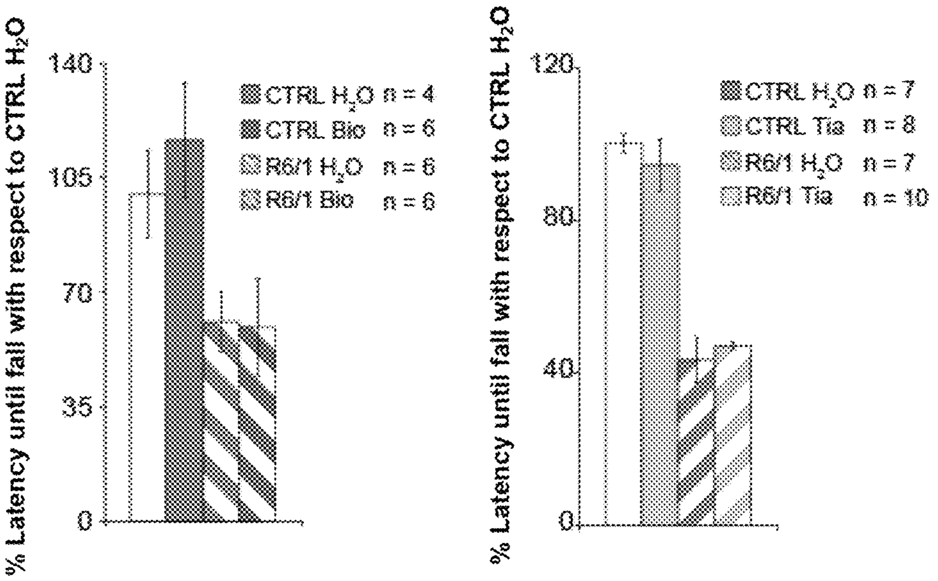
Figure 6C:
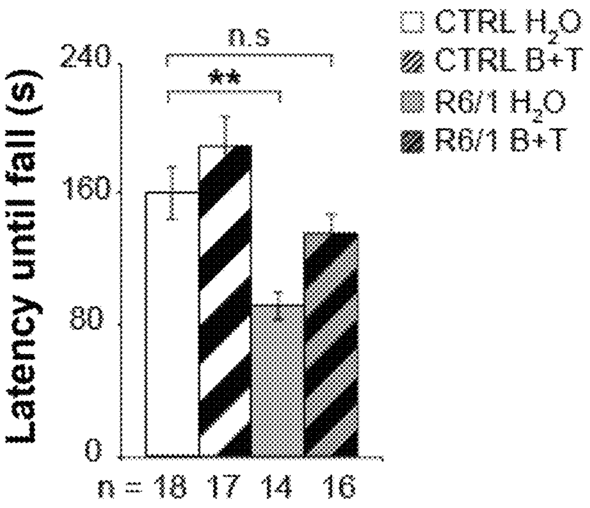

The observed results demonstrate that treatment with biotin or thiamine separately only showed improving trends in some of the behavioural tests (FIG. 6A-B). However, the combined treatment of biotin and thiamine improved the motor coordination deficit in the rotarod test at 18 weeks (FIG. 6C).

Figure 7A:
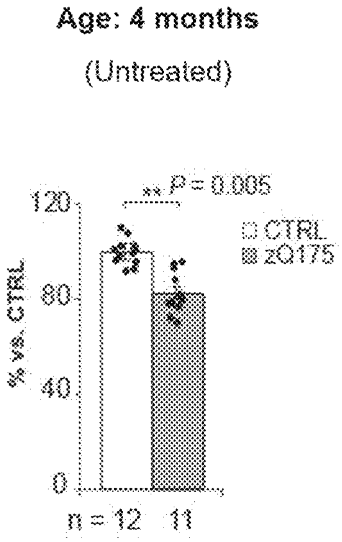
FIG. 7 shows a magnetic resonance analysis of zQ175 mice treated with thiamine and biotin. Magnetic resonance analysis of the striatal volume of zQ175 and WT mice at ages of (A) 4 months (pre-treatment) and (B) 7 months under control conditions ($H_2O$) or treated with biotin and thiamine (B+T). (C) Phosphocreatine levels in striatum of untreated zQ175 mice ($H_2O$) or zQ175 mice treated with biotin and thiamine (B+T), with respect to the untreated WT mice ($H_2O$) analysed by magnetic resonance spectroscopy (MRS).
Figure 7B:
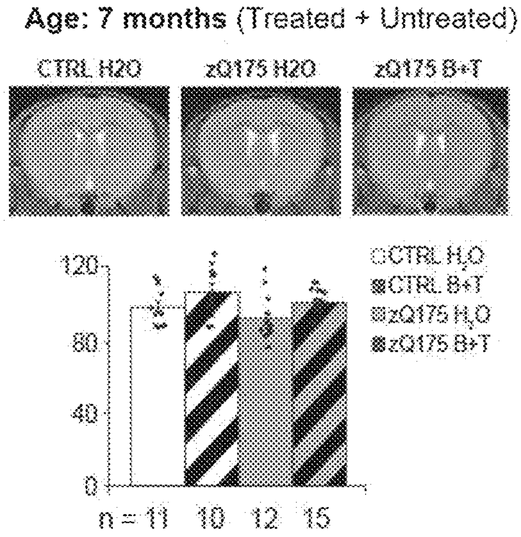
Figure 7C:
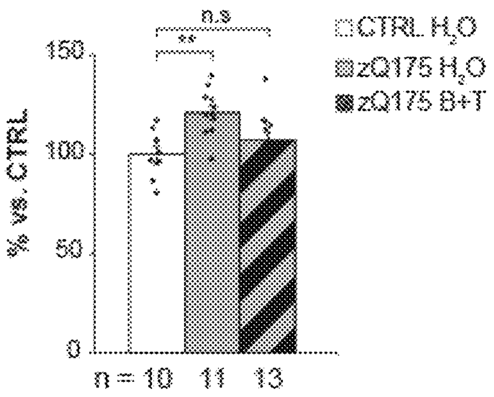

Compared to the transgene of R6/1 mice, the CAG mutation in the heterozygous zQ175 mouse model of HD, which is in the endogenous gene, is more similar to the mutation suffered by subjects with HD, despite not inducing clear motor phenotypes in the mouse's lifetime. However, it is known that heterozygous zQ175 mice show striatal atrophy from an early age (Heikkinen, T., et al. PloS one. 2012: 7, e50717) (FIG. 7A), and in the heterozygous zQ175 mouse model treated with the combined thiamine-biotin therapy described herein, attenuation of the atrophy suffered by the striatum was observed by magnetic resonance brain volumetry after a minimum of three months of administering said combined treatment (FIG. 7B). Heterozygous zQ175 mice also show an increase in striatal phosphocreatine detectable by magnetic resonance spectroscopy (MRS) which is not seen in heterozygous zQ175 mice treated with combined thiamine-biotin therapy described herein (FIG. 7C).

Therefore, the results indicate that mice with HD also show thiamine deficiency in the brain and the motor symptoms of HD, atrophy and increased striatal phosphocreatine improve with the thiamine and biotin-based treatment.

In summary, the results shown in this document demonstrate that decreased SLC19A3 protein levels in subjects with HD correlate with thiamine deficiency in the brain (decreased thiamine in CSF and in striatal TPP), which promotes the usefulness of the treatment of these subjects with vitamin supplements based on a combined administration of thiamine and biotin, which is further supported by the fact that motor symptoms, striatal atrophy and increased striatal phosphocreatine in mouse models of HD improve with the combination of thiamine and biotin-based vitamin supplements.

The invention claimed is:

1. A method for the treatment of Huntington's disease comprising administering to a subject in need thereof an effective amount of a composition comprising biotin and thiamine.

2. The method according to claim 1 wherein the concentration of biotin is at least 0.40 mg/kg/day, and the concentration of thiamine is at least 2 mg/kg/day.

3. The method according to claim 1 wherein the composition further comprises at least one excipient and/or pharmacologically acceptable carrier.

4. The method according to claim 1 wherein the composition further comprises at least one active ingredient.

5. The method according to claim 4 wherein the active ingredient is selected from the list consisting of: tetrabenazine, haloperidol, chlorpromazine, risperidone, quetiapine, amantadine, levetiracetam, clonazepam, citalopram, escitalopram, fluoxetine, sertraline, olanzapine, valproate, carbamazepine, lamotrigine and/or any of the combinations thereof.

6. The method according to claim 1 characterized in that the composition is administered by any of the following routes: oral, sublingual, parenteral, intravenous, intraperitoneal and/or intramuscular route.

7. The method according to claim 6 wherein the route of administration is the oral route.

8. The method according to claim 1 wherein the compounds of said composition are formulated or administered together, separately or sequentially.

9. The method according to claim 1 wherein said composition is repeatedly administered to a subject.

* * * * *